United States Patent [19]
Halliburton

[11] Patent Number: 5,674,232
[45] Date of Patent: Oct. 7, 1997

[54] CATHETER AND METHOD OF USE THEREOF

[76] Inventor: Alexander George Halliburton, 20 Coachman Terrace, Cloverbar Ranch, Edmonton, Alberta, Canada, T8H 1M2

[21] Appl. No.: 716,698

[22] Filed: Sep. 20, 1996

Related U.S. Application Data

[63] Continuation of Ser. No. 285,412, Aug. 13, 1994, abandoned, which is a continuation of Ser. No. 96,384, Jul. 26, 1993, abandoned, which is a continuation-in-part of Ser. No. 533,402, Jun. 5, 1990, Pat. No. 5,368,603.

[51] Int. Cl.⁶ ................................................. A61B 17/22
[52] U.S. Cl. ........................... 606/159; 606/170; 604/22
[58] Field of Search ........................ 606/159, 170, 606/171, 169; 604/22; 128/751, 752, 753, 754

[56] References Cited

U.S. PATENT DOCUMENTS

| | | |
|---|---|---|
| 3,173,414 | 3/1965 | Guillant . |
| 3,289,669 | 12/1966 | Dwyer et al. . |
| 3,401,684 | 9/1968 | Dremann . |
| 3,561,429 | 2/1971 | Jewett et al. . |
| 3,590,808 | 7/1971 | Muller . |
| 3,606,878 | 9/1971 | Kellogg, Jr. . |
| 4,445,509 | 5/1984 | Auth . |
| 4,616,648 | 10/1986 | Simpson . |
| 4,669,469 | 6/1987 | Gifford, III et al. . |
| 4,771,774 | 9/1988 | Simpson et al. . |
| 4,781,186 | 11/1988 | Simpson et al. . |
| 4,819,635 | 4/1989 | Shapiro . |
| 4,994,067 | 2/1991 | Summers . |
| 5,085,662 | 2/1992 | Willard . |
| 5,172,702 | 12/1992 | Leigh et al. . |
| 5,242,460 | 9/1993 | Klein et al. . |

FOREIGN PATENT DOCUMENTS

| | | |
|---|---|---|
| 352872A3 | 3/1985 | European Pat. Off. . |
| 0291170 | 11/1988 | European Pat. Off. . |
| 0582005 | 2/1994 | European Pat. Off. . |
| 1161400 | 8/1958 | France . |
| 1766252 | 4/1968 | Germany . |
| 2453058 | 11/1974 | Germany . |
| 2622850 | 9/1977 | Germany . |
| 3035416 | 6/1982 | Germany . |
| 240923 | 8/1969 | U.S.S.R. . |
| 8905611 | 6/1989 | WIPO . |
| 9002523 | 3/1990 | WIPO . |
| 9112847 | 9/1991 | WIPO . |
| 9214413 | 9/1992 | WIPO . |

OTHER PUBLICATIONS

Altered Fluorescence Emission during Continuous Wave Laser Ablation of Atherosclerotic Plaque by Alexandra Lucas, Richard H. Clarke, Jeffrey M. Isner, 18 pages.

The Characterization of Human Coronary Artery Atherosclerotic Plaque Fluorescence Emission by Alexander Lucas, Markus J. Radosavljevic, Erbin Lu, Edward J. Gaffrey, 26 pages.

(List continued on next page.)

*Primary Examiner*—Michael H. Thaler
*Attorney, Agent, or Firm*—Rodman & Rodman

[57] ABSTRACT

An endarterectomy catheter and method for removing obstructions from an artery comprises a cylindrical, oval, kidney shaped or other shape housing, the housing having an opening inside which a primary shear is movable. The primary shear is razor sharp and cylindrical or other shaped with a smooth or serrated or threaded finish on the inner diameter and movable by means of a firing wire connected by an adapter to a trigger mechanism, which moves the primary shear backward and forward within the housing to excise, encapsulate and store obstructions that protrude into the opening. The primary shear can also be moved by an electric wire and solenoid, hydraulic system or other means. A guide wire positions the catheter in an artery fallopian tube or other lumen and an inflatable saline anchor or anchors stabilize the catheter against the obstruction to execute a precise cut.

20 Claims, 16 Drawing Sheets

OTHER PUBLICATIONS

Correlation of Fluorescence Emission With The Plaque Content and Intimal Thickness of Atherosclerotic Coronary Arteries by Edward J. Gaffney, Richard H. Clarke, Alexandra R. Lucas, and Jeffrey M. Isner, from *Lasers in Surgery and Medicine* 9:215–228 (1989).

Percutaneous Atherectomy Catheters By Eric R. Bates, MD, from *Cardiology Clinis*, vol. 6, No. 3, Aug. 1988, pp. 373–382.

Laser Therapy for Cardiovascular Disease: Current Status and Future Direction by Jeffrey M. Isner, Constance D. Fields, Alexandra R. Lucas, from *Choices in Cardiology*, vol. 2, No. 5, pp. 225–228.

Laser Therapy in the Treatment of Cardiovascular Disease by Jeffrey M. Isner, Alexandra R. Lucas, Constance D. Fields, from *British Journal of Hospital Medicine*, vol. 40, Sep. 1988, p. 172.

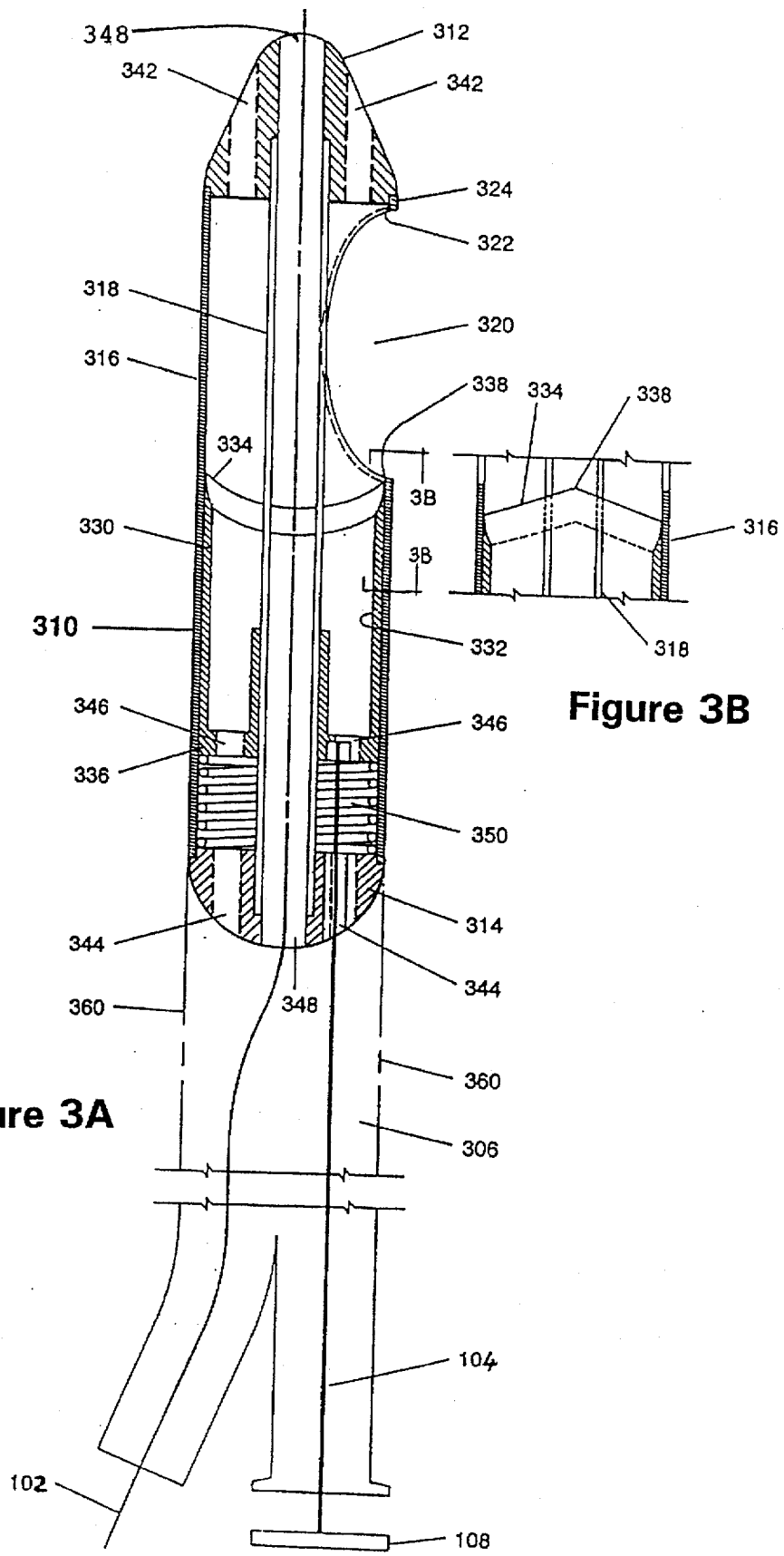

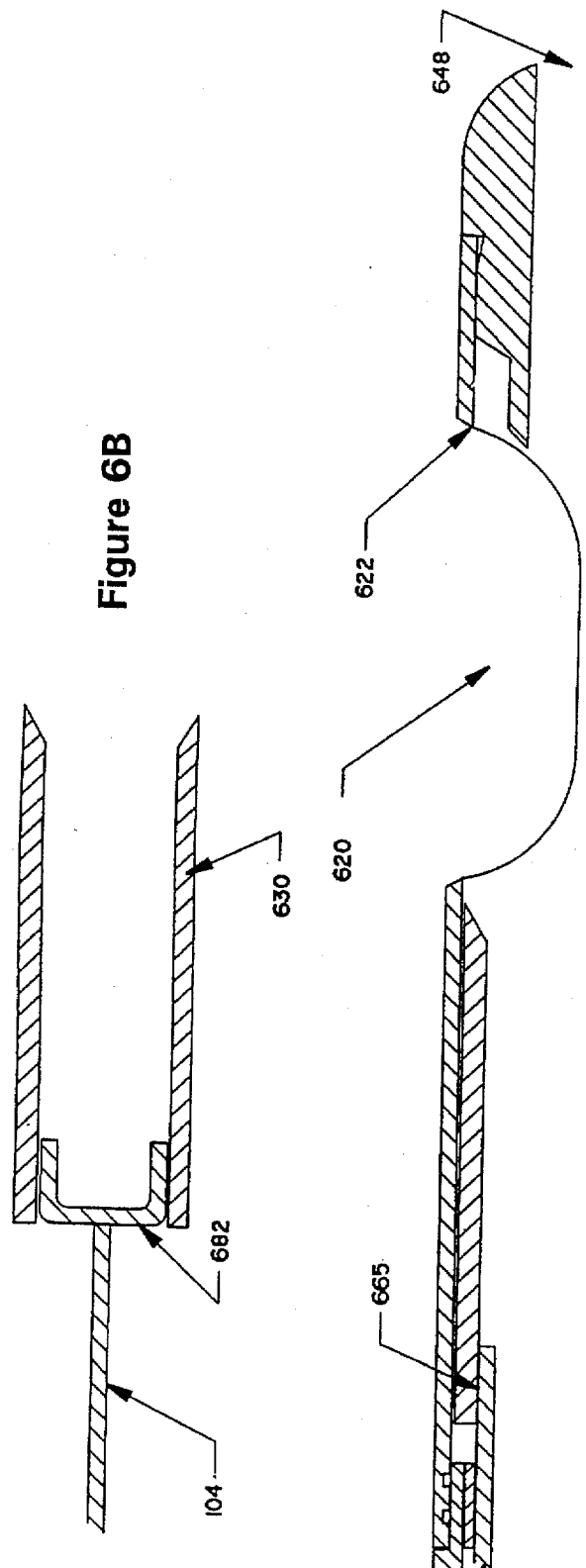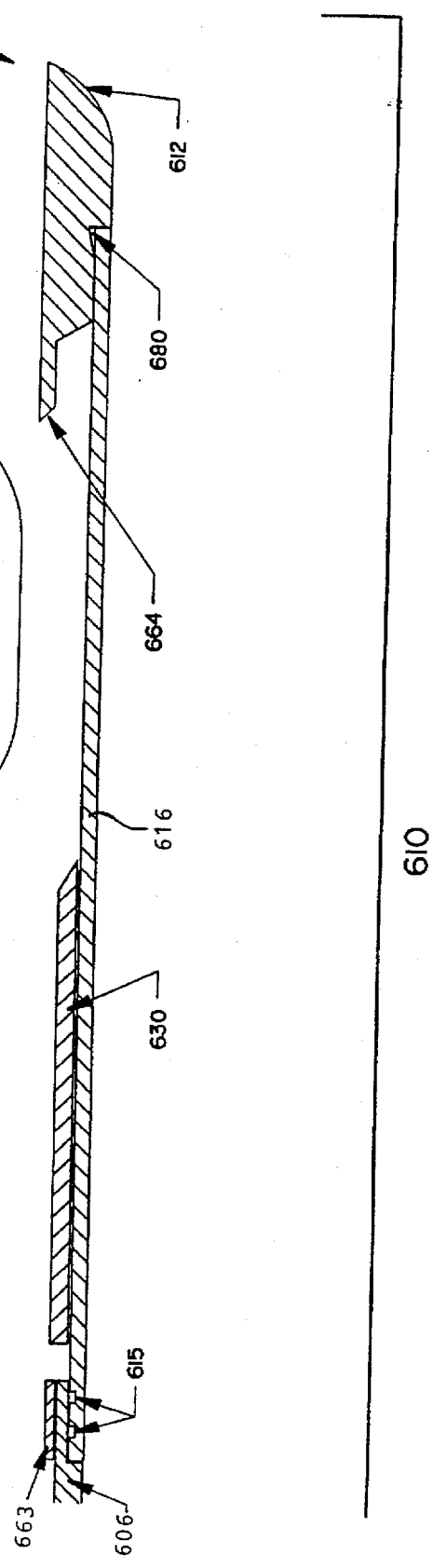
Figure 6B
Figure 6A

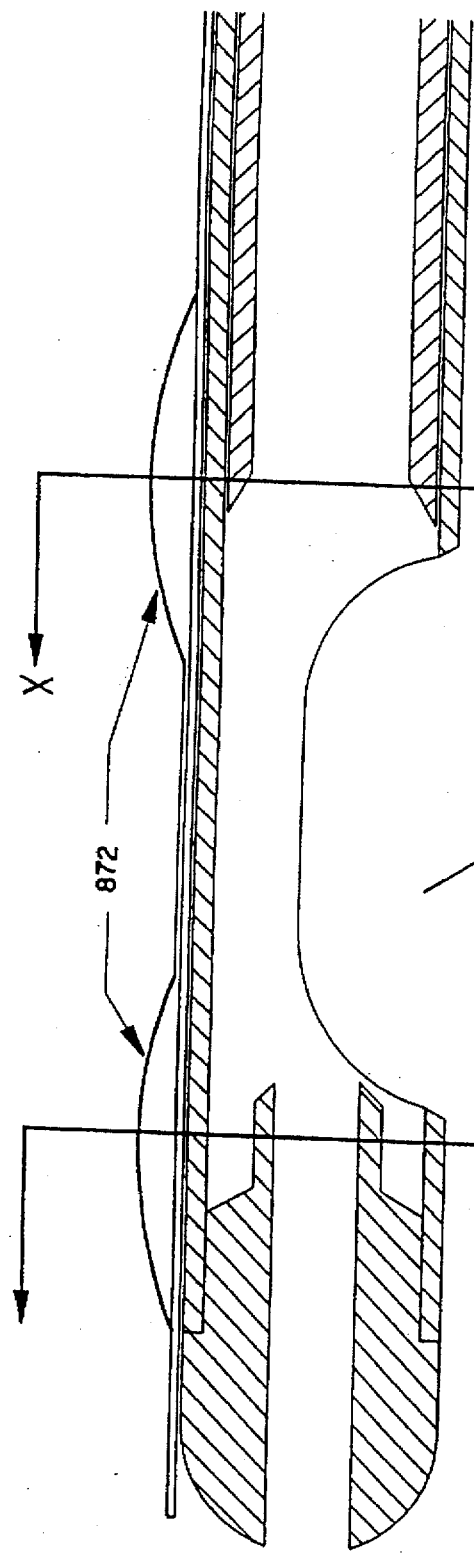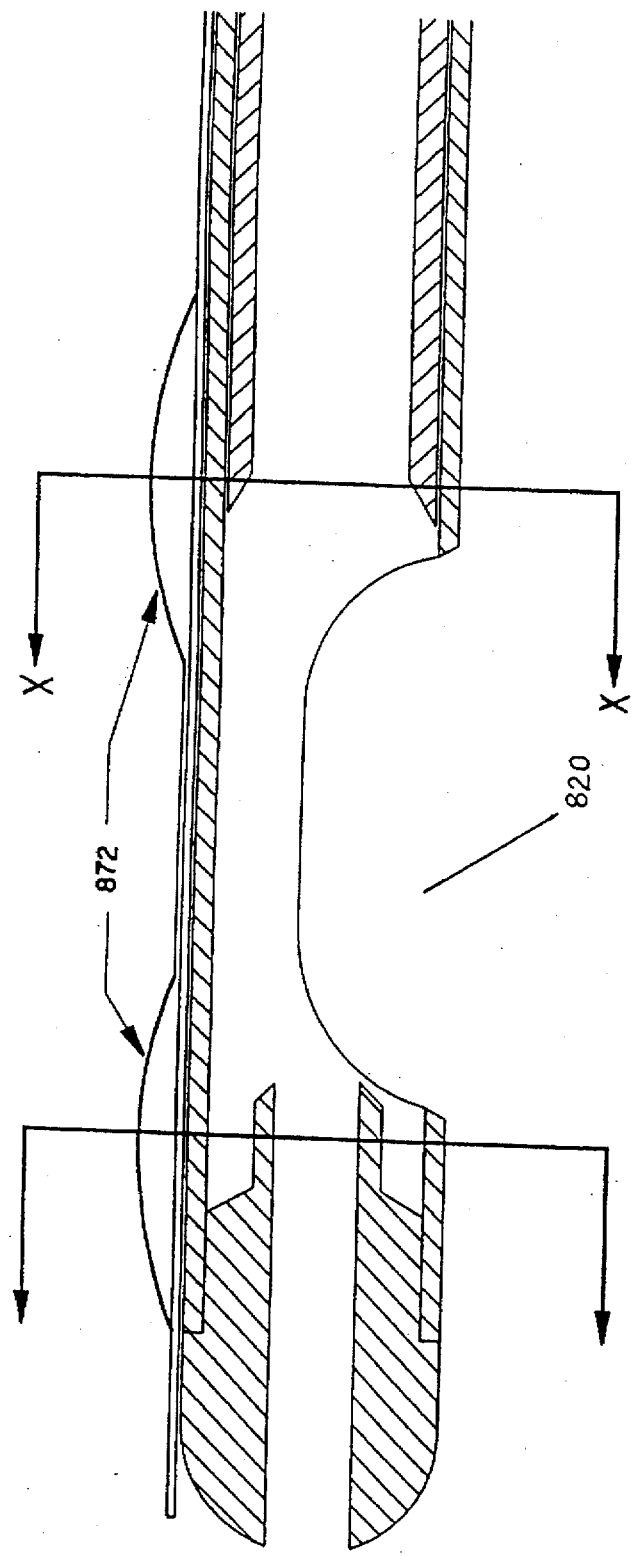
Figure 8A-1
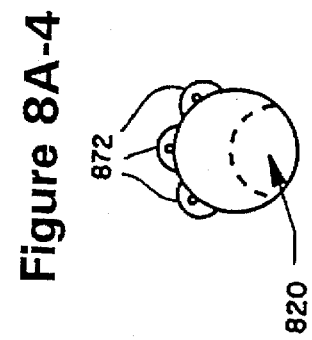
Figure 8A-4
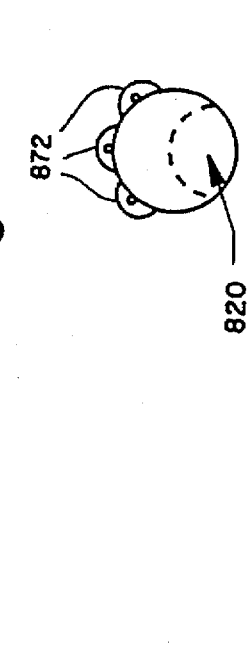
Figure 8A-3
Figure 8A-2

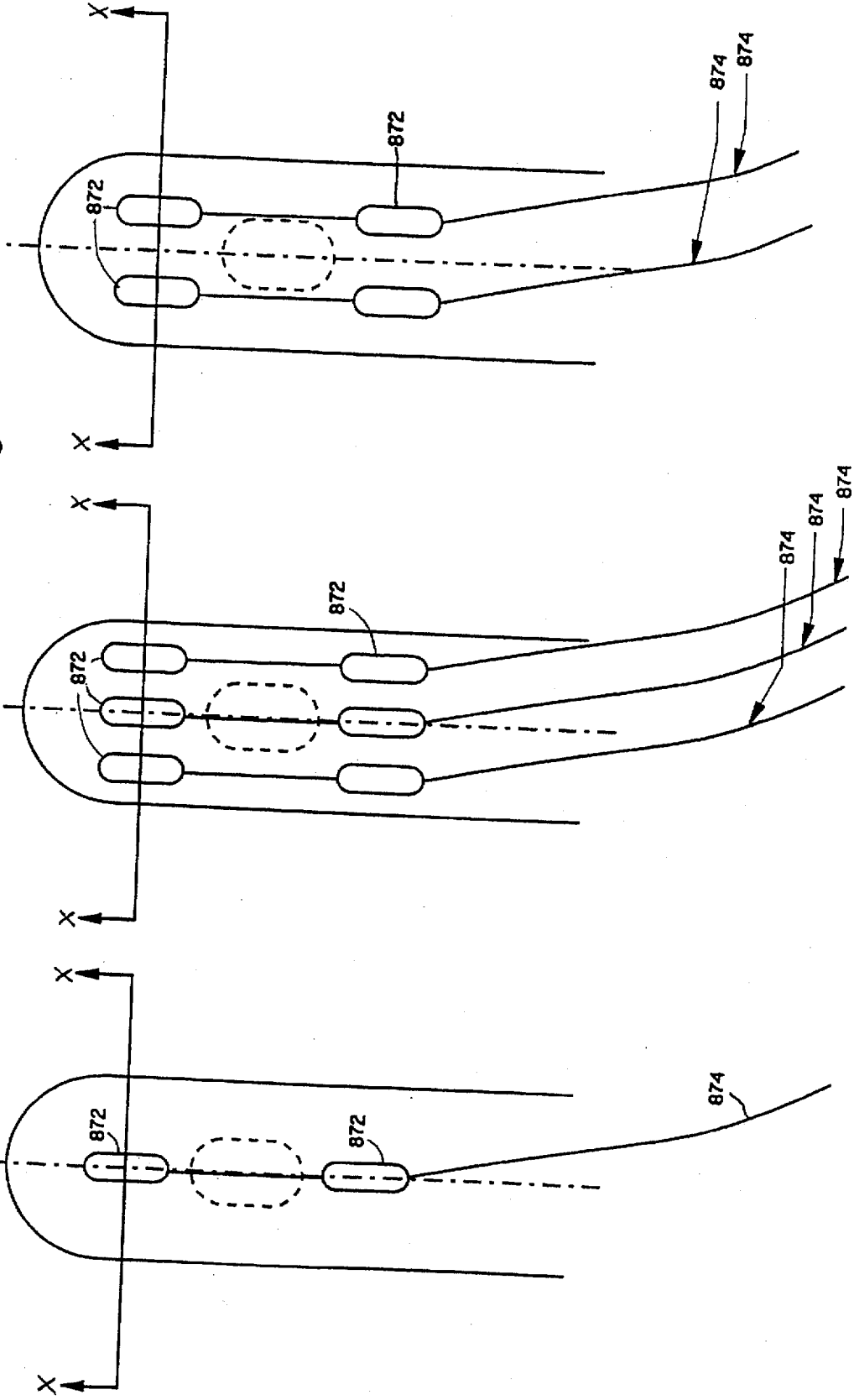

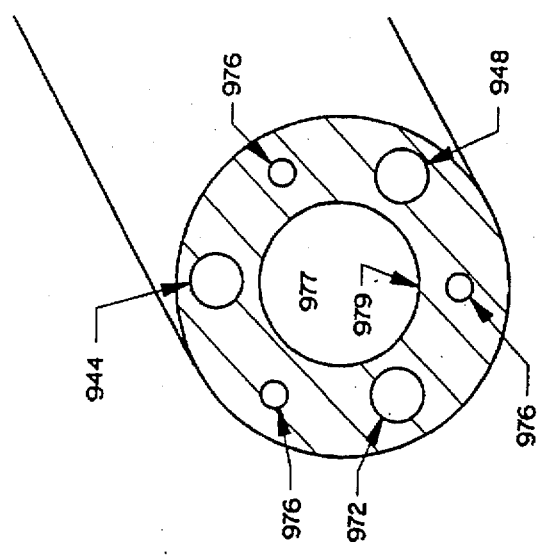
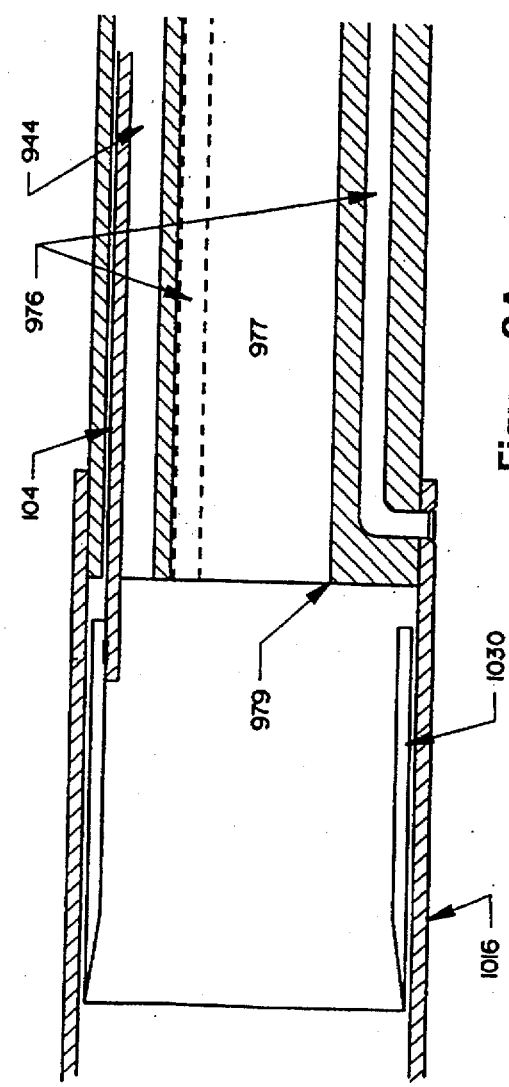

CATHETER AND METHOD OF USE THEREOF

This application is a continuation of application Ser. No. 08/585,412 filed Aug. 3, 1994, now abandoned, which is a continuation of application Ser. No. 08/096,384 filed Jul. 26, 1993, now abandoned which is a continuation-in-part of application Ser. No. 07/533,402 filed Jun. 5, 1990 and now U.S. Pat. No. 5,368,603.

FIELD OF THE INVENTION

This invention is directed to catheters, and to a method of excising obstructions from body channels. In particular, the invention is directed to a catheter and method and may be used in many other applications, like fallopian tubes, to remove obstructions.

BACKGROUND OF THE INVENTION

An endarterectomy or atherectomy catheter is a device that is inserted in an artery to remove plaque from the walls of the arteries. This helps to decrease the risk of heart attacks. In medical terms, an endarterectomy catheter is a device used for the mechanical recanalization of occluded arteries. Occlusions of the vascular lumen may result from atherosclerotic lesions in human coronary arteries resulting in unstable angina and eventual myocardial infarction.

Several atherectomy catheters have been developed but all are relatively complicated and expensive devices. The majority of these devices employ a rotating action to remove obstructions.

Simpson, U.S. Pat. No. 4,781,186, describes a double chambered Catheter with a rotating cutting blade. The distal end of the catheter consists of a solid cylindrical blade in a longitudinal housing with a longitudinal window over a third of its circumference. The window is on one side and a balloon is on the other side of the catheter. The housing and the rotating blade are made of stainless steel. The blade is attached to a torque cable in one of the catheter chambers. This chamber is also used to inject fluid or contrast media into the artery. The other chamber is used for balloon inflation. A short terminal fixed guide wire assists in positioning the window towards the atherosclerotic lesion. The cutting blade is then activated by a hand held motor at 2,000 rpm and the blade is rotated against the lesion. Excised plaque is trapped inside the catheter. A separate mechanism is used for balloon inflation. Other related patents for the Simpson atherectomy catheter are European application 352,872, U.S. Pat. Nos. 4,771,774; 4,669,649; and 4,616,648.

Auth, U.S. Pat. No. 4,445,509 describes a catheter having a rotating abrasive burr that can be advanced over a movable guide wire. The burr rotates at 150,000 rpm or higher and is driven by a compressed air turbine. The turbine also pumps a saline solution to cool the fast moving parts.

Theratek International of Miami, Fla., provides a single lumen flexible polyurethane catheter (also called the Kensey atherectomy catheter), having a rotating metallic cam at the distal end which is driven at 100,000 rpm to emulsify the targeted lesion.

Ultramed, Inc. of San Diego, Calif., provides a transluminal extraction endarterectomy catheter having a rotating steel cutting blade. The blade rotates at high speed, 750 rpm, to excise the targeted lesion. A vacuum is used to retrieve the debris from the lesion.

SUMMARY OF THE INVENTION

The inventor has provided a simplified catheter that does not require high speed rotating blades or drills, and a method of excising obstructions from an artery that may be stored in a reservoir and removed from the body. The catheter of the present invention has further been found to be generally useful in removal of obstructions from body channels including arteries, fallopian tubes and lumen. The catheter of the present invention mechanically removes obstructions by means of the shearing action of a blade or between a blade and the sharpened edge of the housing. Thus in one embodiment, there is provided a catheter for excising obstructions from within a body channel comprising:

a housing adapted for entry into the channel, the housing having an opening for accepting an obstruction;

a primary shear disposed within the housing and moveable across the opening;

an urging means connected to the primary shear and operable from outside the body channel for urging movement of the shear in the housing and across the opening to create a guillotine action; and, means for locating the housing in the channel.

In another embodiment there is provided a catheter for excising obstructions from within a body channel comprising:

a housing adapted for entry into the channel, the housing having a nose end, a rearward end continuous with a communicating tube for allowing communication with the housing from outside of the body channel and an opening therebetween for accepting an obstruction;

a cylindrical substantially hollow primary shear disposed within the housing and moveable across the opening;

an urging means connected to the primary shear and operable from outside the body channel for urging the shear to move within the housing and across the opening to create a guillotine action, the urging means being in the form of a tube connected about a radius of the shear and being disposed within the communicating tube; and, means for locating the housing in the channel.

An inflatable anchor may be attached to the housing to maintain the housing in position in the body channel. The anchor may consist of any number of fluid fillable bladders to secure the catheter against the obstacle to produce a precise cut, a smooth finish close to artery wall, while locating the housing within the artery.

The endarterectomy catheter may further include means for collecting fragments of an obstruction that has been cut by the primary shear. Those means may include a packing stub at the forward end and a hollow tube behind the shear to act as a collection reservoir and as an urging means.

The catheter housing is preferably substantially cylindrical and the primary shear is preferably hollow, substantially cylindrical and snugly fitted within the housing to create, along with the edge of the opening, a pair of opposing shearing surfaces.

In a further embodiment, the endarterectomy catheter housing includes an inner tubular section extending from the forward end to the rearward end, and an outer tubular section extending from the forward end to the rearward end, the inner tubular section being fitted within the outer tubular section, and the primary shear being disposed between the inner tubular section and the outer tubular section.

In a still further embodiment, the opening extends fully around the housing.

In further embodiments, the forward edge of the opening, or all of the opening, may have a sharpened edge to assist in the guillotine action of the primary shear, the shear can be operated by the same firing mechanism or spring action. hollow tube which would permit storage of plaque in a type of reservoir, the housing may be flexible to allow for ease of positioning of the housing and the housing may be provided with openings in its forward and rearward ends to allow body fluids to flow through the catheter while it is in operation.

In a broad aspect of the present invention there is provided a catheter system for excising obstructions from within a body channel comprising:

a housing adapted for entry into the channel, the housing having an opening for accepting an obstruction;

a primary shear disposed within the housing and moveable across the opening;

a communicating means connected to the primary shear and operable from outside the body channel for urging the shear to move within the housing and across the opening to create a guillotine action;

a triggering means for triggering the communicating means to urge the shear movement from a location external of the body channel; and means for locating the housing in the channel.

In one embodiment of the method of the invention, there is provided a method of excising an obstruction from a body channel, the method comprising:

locating a housing within the body channel adjacent an obstruction, the housing having an opening for accepting an obstruction and a shear moveable across the opening;

positioning the housing such that the obstruction protrudes into the opening of the housing;

urging the shear across the opening to excise at leat part of the obstruction with a guillotine action; and, removing the housing from the body channel.

The advantages of using the catheter over the prior art devices include: the primary cutting edge cleaves the obstruction cleanly from the channel wall and entraps the debris within the serrated finish of the inside diameter of the primary shear; there is no high speed rotating object in the cavity that can otherwise damage the cavity; there is no heat build up through operation of the cutting edge; no cooling mechanism is required; no vacuum is required to remove the fragments of the obstruction since all tissue may be collected in tube reservoir; removal of tissue from the reservoir may be accomplished through syphoning by syringe; and, no motor or complex support system is required.

BRIEF DESCRIPTION OF THE DRAWINGS

There will now be described preferred embodiments of the invention, with reference to the drawings, by way of illustration, in which like numerals denote like elements and in which:

FIG. 3A is a longitudinal section of another embodiment of a housing according to the invention;

FIG. 3B is a section along the line 3B—3B of FIG. 3A;

FIG. 6A is a detailed longitudinal section of another embodiment of a housing according to the invention;

FIG. 6B is a longitudinal section through a shear having a base clamp to accommodate attachment to the firing wire;

FIG. 8A is a longitudinal section of embodiments and corresponding cross-sections of an inflatable saline anchor, which are to be used with other embodiments of the invention;

FIG. 8B is a series of plan views of embodiments of inflatable saline anchor;

FIG. 9 is a cross-section of an extruded tube as is also shown in longitudinal section attached to a housing;

DESCRIPTION OF PREFERRED EMBODIMENTS

In this patent, a shear is the cutting means or blade used to cut through an obstruction using a slicing action referred to as a guillotine action.

While often in this patent the use of the present invention is taught for removal of obstructions from arteries, generally material may be removed from any body channel such as an artery, fallopian tube or lumen, whether it be a fatty, fibrous or calcified tissue deposition (known for example as atherosclerotic plaque, atheroma or lesion), which will be referred to as the obstruction.

A description of methods and apparatus currently used for the removal of obstructions may be found in the *Textbook of Interventional Cardiology*, Edited by E. J. Topol, Saunders, Philadelphia, 1990.

PHYSICAL CONFIGURATION

Preferred embodiments of the invention will now be described.

Figure 1:
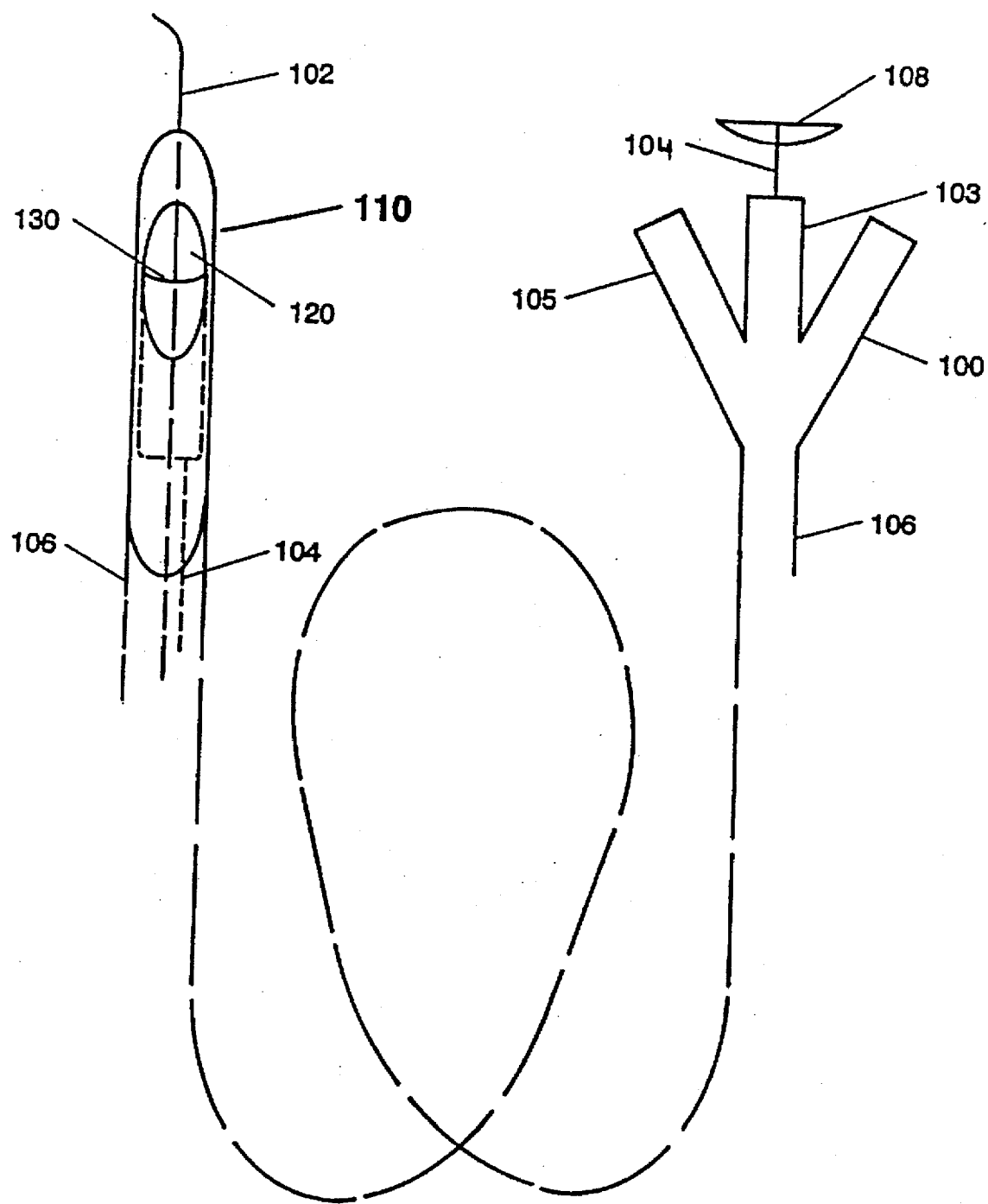
FIG. 1 is a perspective of an embodiment of a catheter according to the invention with a cable connection to the catheter; and includes firing mechanism.

Referring to FIG. 1, there is shown a perspective view of a catheter according to the invention. A housing 110, including an opening 120 and primary shear or blade 130, is connected to urging means such as cable or firing wire 104 for moving the primary shear 130 in the housing 110 across the opening 120. Means such as guide wire 102 for locating the housing 110 in an artery may pass through the housing 110, or in an alternative embodiment be transferred through a lumen of an extruded tube. Both the guide wire 102 and cable 104 are capable of sliding within at least one sleeve 106. The opening 120 is preferably oval being slightly elongated in the longitudinal direction, and should be sufficiently large to receive at least part and preferably all of an obstruction. The cable or firing wire 104 exits the sleeve 106 at port 103 and is preferably operated manually from outside the artery by trigger 108 to move the primary shear 130 reciprocally backward and forward within the housing 110 across the opening 120. The guide wire 102 exits the sleeve 106 at port 105. A port 100 for injecting material into or withdrawing material from the housing or artery along the sleeve is also provided.

Twelve embodiments of the invention will be described here with reference to FIGS. 2A, 2B, 3A, 3B, 4A, 4B, 5, 6A, 6B, 7, 8A, 8B, 9, 10, 11, 12 and 13. In each case, but FIGS. 6, 7, 9, 11, 12 and 13 the same guide wire 102 is used, together with sleeve 106, trigger 108 and pods 100, 103 and 105. The main difference between the embodiments shown in these figures is the construction of the housing, the primary shear and the opening and these will be described in some detail. Embodiments of an anchoring system, extruded tubing and triggering mechanism will also be described. A further embodiment using an electrical wire and solenoid arrangement or hydraulic actuation means for the shear, has not been shown in any of the figures.

Figure 2A:
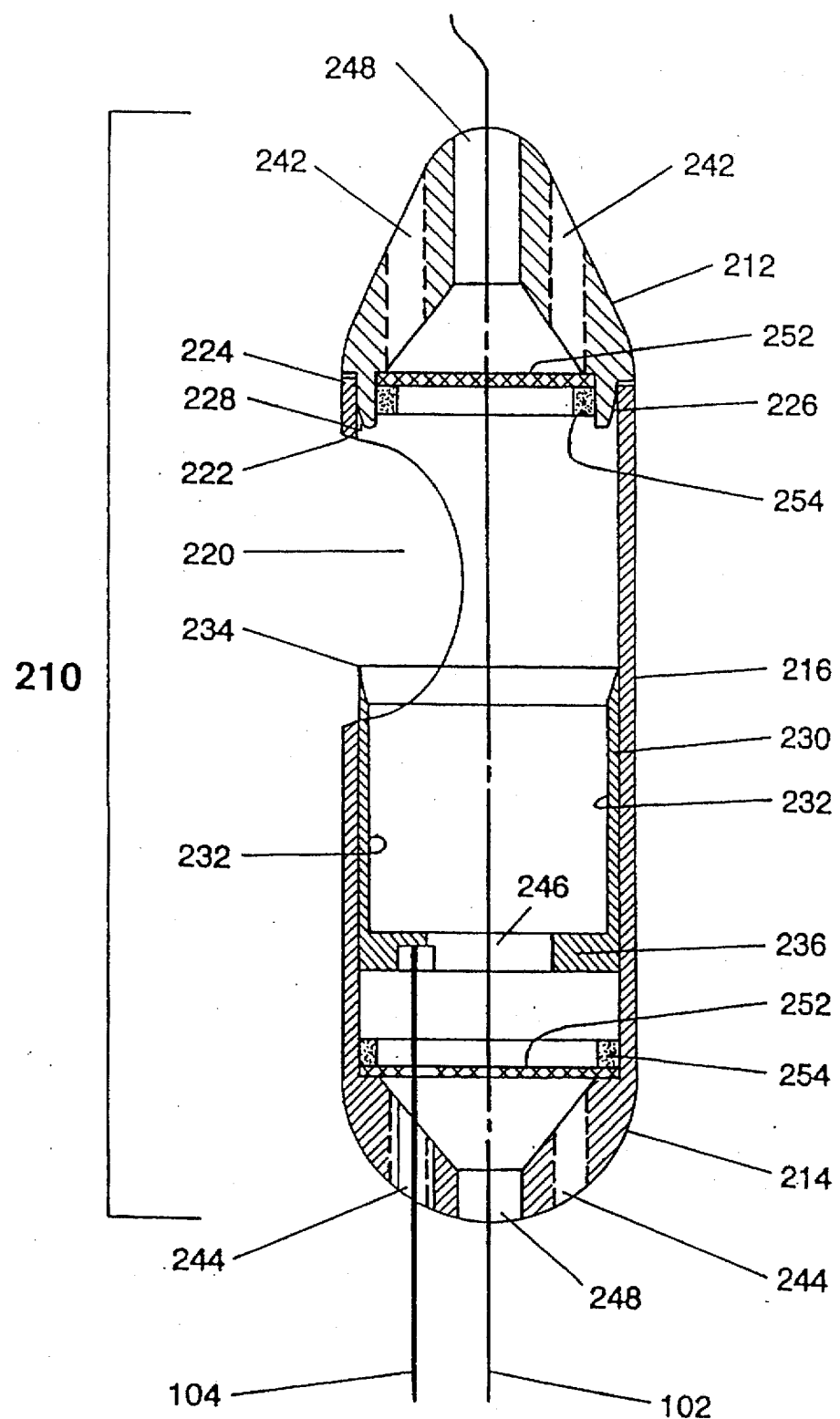
FIG. 2A is a longitudinal section of one embodiment of a housing according to the invention.
Figure 2B:
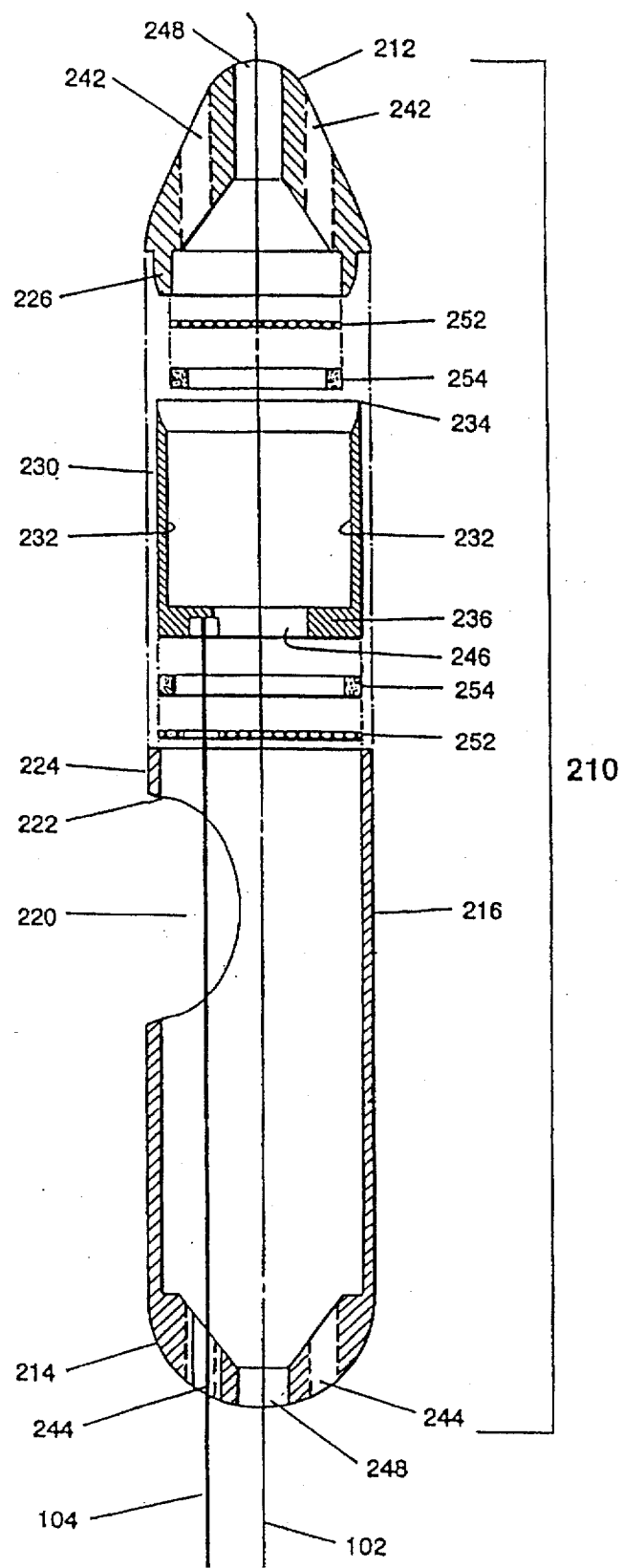
FIG. 2B is an exploded longitudinal section of the housing of FIG. 2A.

An embodiment of the catheter as shown in FIGS. 2A and 2B comprises housing 210 including a forward nose end 212 and a rearward end connected by a tubular section 216. The tubular section 216 defines a substantially oval opening 220. Apertures 242 and 244 in the forward and rearward ends respectively allow blood to pass through the housing 210. Guide wire 102 passes through openings 248 in the housing 210.

The primary shear 230 is hollow and substantially cylindrical with sides 232 and a cylindrical hollow ground cutting edge 234, (ie. "Slide Fit"). The primary shear 230 is adapted to fit snugly within the housing 210, and is movable backwards and forwards within the housing 210 across the opening 220 under control of the firing wire 104, which is attached by any suitable means to the base portion 236 of the primary shear 230. At the forward extent of the primary shear 230 (upon movement of the primary shear 230 within the housing 210), the edge 234 is preferably sheathed within the housing 210 beneath a lip 224, and the opening 220 is completely blocked by the cylindrical sides 232 of the primary shear 230. The primary shear 230 may be viewed as a circular blade that has been adapted to the shape of the housing, and sheathed within the housing, so that it is substantially only movable reciprocally across the opening, thus not requiring any rotary motion to excise the obstruction. The hollow, cylindrical interior walls 232 of the shear 230 have a smooth or preferably serrated, threaded or roughened surface to snag debris which constitutes a means for collecting fragments of an obstruction. Thus in operation the excised part of the obstruction is encapsulated, facilitating removal of the excised part of the obstruction from the artery or allowing multiple cuts where debris passes along the hollow shear 230 to a hollow tube reservoir formed in the housing 210 or toward the base 236 of the hollow shear 230.

The cutting edge 234 of the primary shear 230 is preferably bevelled on the inside only as shown in FIGS. 2A and 2B, such that the cutting edge 234 is as close to the inside wall of the tubular section 216 as possible. The bevelled portion of the cutting edge 234 is preferably hollow ground (concave) to render the edge as sharp as possible, though it may be straight. The cutting edge 234 may also be spiked to form a trocar like body with a point or spike, as described in more detail in relation to FIGS. 3A and 3B, such that the point may affix or spear the obstruction before piercing and excising it.

The firing wire 104 passes through one of the apertures 244 in the rearward end 214 of the housing 210 and is attached to the shear 230 at preferably adjacent the base portion 236. The shear 230 is moved along the housing 210 by pushing or pulling with the wire 104 through the trigger (not shown). The boundaries of the opening 220 are preferably sharpened to form a secondary shear 222 to assist the cutting action of the primary shear 230. The secondary shear 222 assists particularly in holding the targeted obstruction in place while the action of the primary shear 230 is responsible for most of the cutting action. The slide fit of the primary shear 230 within the housing 210 is important in creating an effective cutting surface at the base of the obstruction close to the wall of the artery.

As shown in FIGS. 2A and 2B, an interior lip 226 is formed on the forward nose cone 212 around the circumference of the housing 210 adjacent the secondary shear 222. The interior lip 226 and lip 224 provide a notch 228 into which the cutting edge 234 of the primary shear 230 fits upon completion of the shearing action. The close fit of the notch 228 with the cutting edge 234 helps to ensure that the obstruction is completely severed from the artery wall. This feature can be important in the case of some particularly resilient obstructions.

An opening 246 in the rearward end of the primary shear 230 allows blood to flow through the primary shear 230. Screens 252 may be provided in the forward and rearward end caps 212 and 214 respectively to catch any fragments of the obstruction that escape encapsulation by the hollow tube reservoir in the primary shear 230 or housing. The screens 252 may be secured by lock washers 254. If desired, the lock washers may be omitted and the screens 252 press fitted into place.

Referring to FIGS. 3A and 3B, there is shown a further embodiment of a catheter according to the invention. The embodiments of FIGS. 3A and 3B is complex to manufacture and thus is not a preferred embodiment. In this embodiment, the housing 310 comprises a rearward end 314, a forward end 312, an outer tubular section 316 and an inner tubular section 318. The inner tubular section 318 is located centrally within the outer tubular section 316 and is hollow to allow blood to pass through the housing 310. Additionally apertures 342 and 344 in the forward and rearward ends respectively allow blood to pass through the housing 310. Guide wire 102 passes through openings 348 in the forward and rearward ends of the inner tubular section.

Although blood may pass through the embodiments of the housing shown, for most applications the catheter guide wire 102 and cable 104 combination sheathed within one or more plastic sleeves will block the passage of blood during treatment. In such cases, autoperfusion methods as described at page 454 of the *Textbook of Interventional Cardiology*, referred to earlier in this patent, may be used to allow blood to flow during the use of the catheter. In such methods, small holes 360 are formed in the sleeve 306 and the blood may pass into, along and out of the sleeve 306.

The primary shear 330 slides along the inner tubular section 318 and is hollow and substantially cylindrical having sides 332 and base portion 336. The base portion 336 includes small apertures 346 to allow blood to pass through the shear 330 while preventing the passage of excised obstruction. The shear 330 is manipulated by the wire 104. The outer tubular section 316 defines an opening 320. The opening 320 is formed similarly to the opening 220. The edge of the opening is sharpened, preferably hollow ground, to form a secondary shear 322 and is extended adjacent the nose end 312 to form a lip 324.

In this embodiment, a compression spring 350 is provided to urge the primary shear 330 forward from the position shown in FIG. 3A to a forward position (not shown, but the equivalent position is shown in ghost outline in FIG. 2A) in which the cutting edge 334 of the primary shear 330 is sheathed beneath lip 324. A guillotine action occurs upon movement of the primary shear 330 into contact with the secondary shear 322, which will excise any obstruction protruding into the opening.

The primary shear 330 is sharpened in the radial direction to form an edge 334 for shearing an obstruction. The cutting edge 334, with reference to FIGS. 3A and 3B, forms a point or spike 338 in the circumferential direction. The spike 338 may be formed on both sides of the primary shear 330, so that the spike 338 may be available for piercing even upon rotation of the primary shear 330 within the housing 310. If desired, the primary shear 330 and the tubular section 316 may be slotted or keyed (not shown) so that the primary shear 330 is guided linearly along the longitudinal axis of the tubular section 316 and prevented from any rotation. The spring 350 may be operated using the cable 104 and a suitable catch on or near the trigger 108 for operating the cable 104. The cable 104 may be pulled backward so that the primary shear 330 moves rearward in the housing 310 to compress the spring 350. The spring 350 may be held in place by a suitable catch and the catch released when it is desired to excise an obstruction. The catch may be any suitable catch for holding a compressed spring. For example, the catch may be a button on the cable 104 that slips into a recess in the plastic sheath 306 adjacent the trigger 108 when the trigger 108 is fully pulled back. To release the spring 350, the button is pushed in.

Figure 4A:
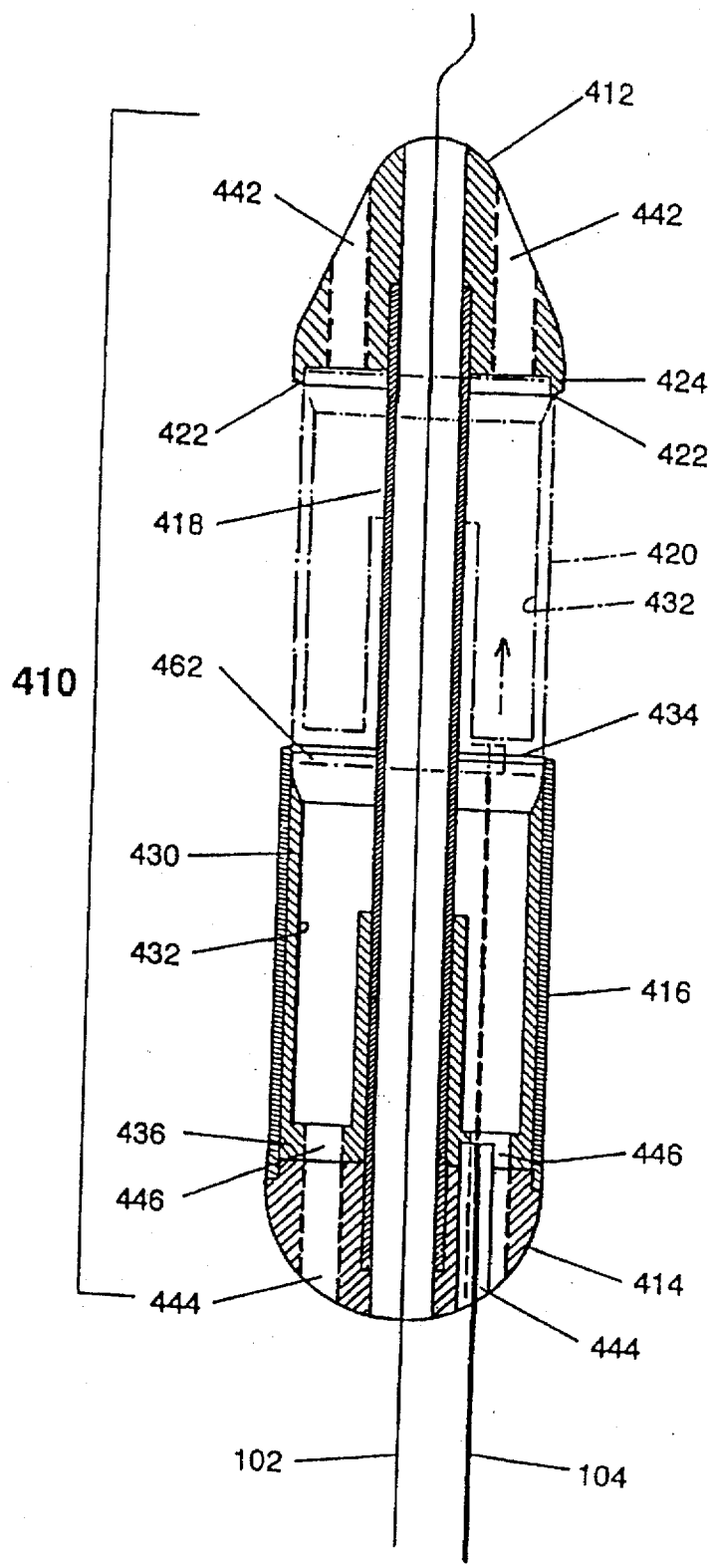
FIG. 4A is a longitudinal section of another embodiment of a housing according to the invention.
Figure 4B:
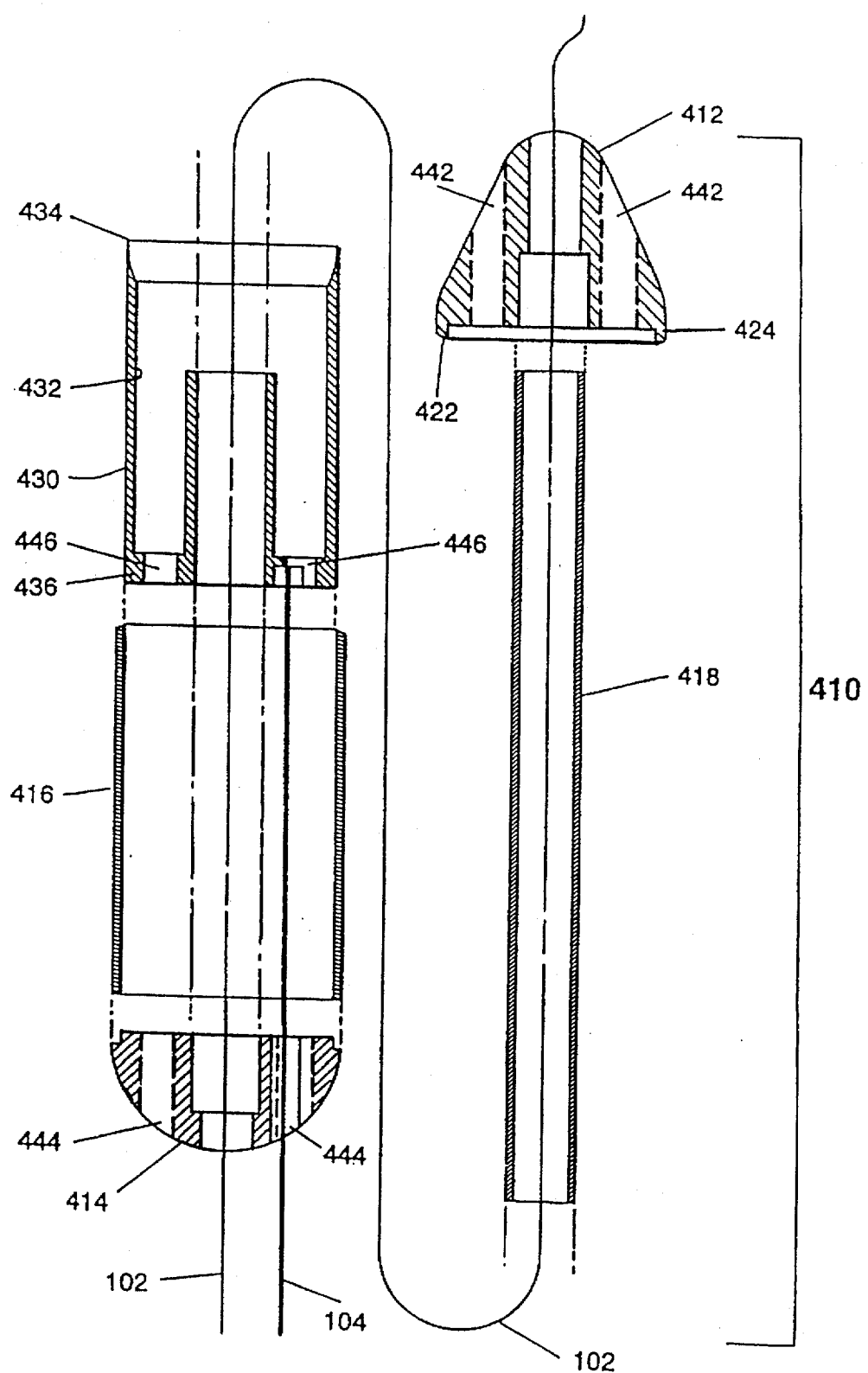
FIG. 4B is an exploded longitudinal section of the housing of FIG. 4B.

FIGS. 4A and 4B show a further embodiment of the invention, in which housing 410 includes rearward end cap 414, a forward nose cone 412, an outer tubular section 416 and an inner tubular section 418. The outer tubular section 416 is concentrically located about the inner tubular section 418 and the inner tubular section 418 extends beyond the outer tubular section, thereby forming an opening 420 that extends fully around the housing 410 between the outer tubular section 416 and the forward nose cone 412. The inner tubular section 418 is preferably hollow to allow for the insertion of the guide wire 102 and to allow for the passage of blood through the housing 410 during operation of the catheter. Apertures 442 and 444 in the nose cone and rearward ends respectively also allow blood to pass through the housing 410. As with the embodiment shown in FIGS. 3A and 3B, autoperfusion techniques may be required to allow blood to pass the sleeve attached to the catheter.

As shown in FIG. 4A, primary shear 430 is slidably mounted on the inner tubular section 418 and is movable from a first, rearward, position in which the primary shear 430 is fully retracted in the outer tubular section 416 to a second, forward, position shown in ghost outline. In the second position, the cylindrical sides 432 of the primary shear 430 completely block the opening 420 and the cutting edge 434 of the primary shear 430 is sheathed in the lip 424 of the nose cone 412.

The primary shear 430 is hollow and substantially cylindrical with cylindrical sides 432 and sharp cutting edge 434 similar to the cutting edge described above in relation to FIG. 2A and 2B. The primary shear 430 has one or more apertures 446 in its base portion 436 to allow blood to pass through the primary shear 430. The openings should preferably be sufficiently small to prevent excised parts of the obstruction from entering the blood stream.

The edge of the nose cone 412 adjacent the opening 420 is preferably sharpened to form a secondary shear 422 to assist the guillotine action of the primary shear 430. The primary shear 430 is operated by the cable 104 which passes through an aperture 444 in the rearward end 414 and connects to the primary shear 430 adjacent an opening 446 in the shear. The cable 104 in turn is operated by a trigger (not shown) but as described hereinabove. The secondary shear 422 is preferably hollow ground as shown at 462 to create an extremely sharp cutting edge.

Figure 5:
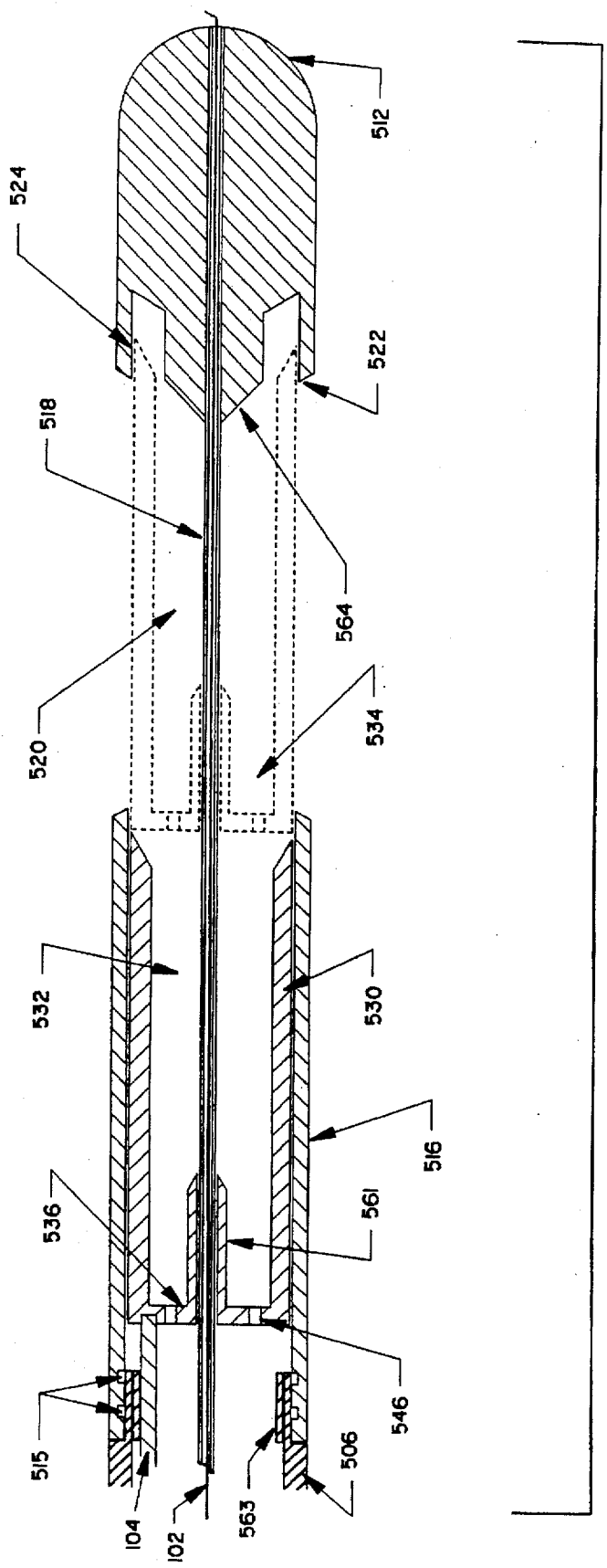
FIG. 5 is a longitudinal section of another embodiment of a housing according to the invention.

FIG. 5 shows a further embodiment of the invention, in which housing 510 includes a forward nose cone 512, an outer tubular section 516 and an inner tubular section 518. The outer tubular section 516 is concentrically located about the inner tubular section 518 and the inner tubular section 518 extends beyond the outer tubular section, thereby forming an opening 520 that extends fully around the housing 510. The inner tubular section 518 is preferably hollow to allow for the insertion of the guide wire 102 and to allow for the passage of blood through the housing 510 during operation of the catheter. As with the embodiment shown in FIGS. 3A and 3B, autoperfusion techniques may be required to allow blood to pass the sleeve attached to the catheter.

Primary shear 530 is mounted by a hollow bush on the inner tubular section 518 and is movable from a first, rearward, position in which the primary shear 530 is fully retracted in the outer tubular section 516 to a second, forward, position shown in ghost outline in FIG. 5. Hollow bush 561 prevents cocking of the shear 530 during movement along the inner tubular section 518. In the second position, the cylindrical sides 532 of the primary shear 530 completely block the opening 520 and the cutting edge 534 of the primary shear 530 is sheathed in the lip 524 in the forward nose end 512 of the housing 510.

The primary shear 530 is hollow and substantially cylindrical having cylindrical sides 532 and sharp cutting edge 534 similar to the cutting edge described above in relation to FIG. 2A and 2B. The primary shear 530 has one or more apertures 546 as previously described in base portion 536.

The boundaries of the opening 520 are preferably sharpened to form a secondary shear 522. The primary shear 530 is operated by the firing wire 104 which connects to the base portion 536 of primary shear 530. The wire 104 in turn is operated by a trigger mechanism such as in FIG. 12.

The embodiment of FIG. 5 differs from those previously described in that there is no rearward end cap. The housing embodiment described in regards to the prior Figures has been extended to be continuous with the sleeve 506. Recesses 515 are formed in the housing for crimping connection between the sleeve and the housing with bush 563. The housing 510 is advanced along the artery by pushing the tube 506. The sleeve 506 may be simply plastic to allow protection for firing wire 104 and guide wire 102 or may be modified to braided cable or extruded tubing to enhance the use of the invention. The continuous sleeve/housing arrangement allows for more access to the catheter during use.

FIG. 6A shows a further embodiment of the invention in which housing 610 includes a nose end 612 and a tubular section 616. The housing 610 is adapted at 615 to crimp by bush 663 onto the braided wire or extruded tubing 606. To strengthen the housing, nose cone 612 includes a recess 680 to permit a secure crimp between the nose end 612 and the tubular section 616.

The nose cone includes a packing stub 664. The stub 664 acts to push and pack the plaque further into the housing once removed. The catheter may be used repeatedly before removing the plaque. The stub 664 takes the form of a rearward extension of the nose cone which fits with the cylindrical shear 630. The opening 620 on the tubular section 616 is enlarged. The catheters of the present invention may have a choice of firing wire attachment. In FIG. 6B, a base clamp 682 is shown for attachment of the firing wire 104 to the shear 630. The base clamp 682 acts to stabilize and prevent cocking of the shear. The force inserted by the firing wire is distributed by the clamp evenly over the circumference of the shear. The firing wire 104 may also be simply attached to the inside of the shear 630 as shown in FIG. 6A. A hollow bush (not shown) may be welded, glued or swaged to the rearward end of shear 630 to accept the firing wire 104.

The embodiment of FIG. 6A is comprised of six parts, however, the housing can be moulded in impregnated plastic which can realistically decrease the number of working parts to three. The use of plastic impregnated with excess carbon or KEVLAR™ allows the embodiment to be reduced to a unitary housing, a shear and a firing wire.

Figure 7:
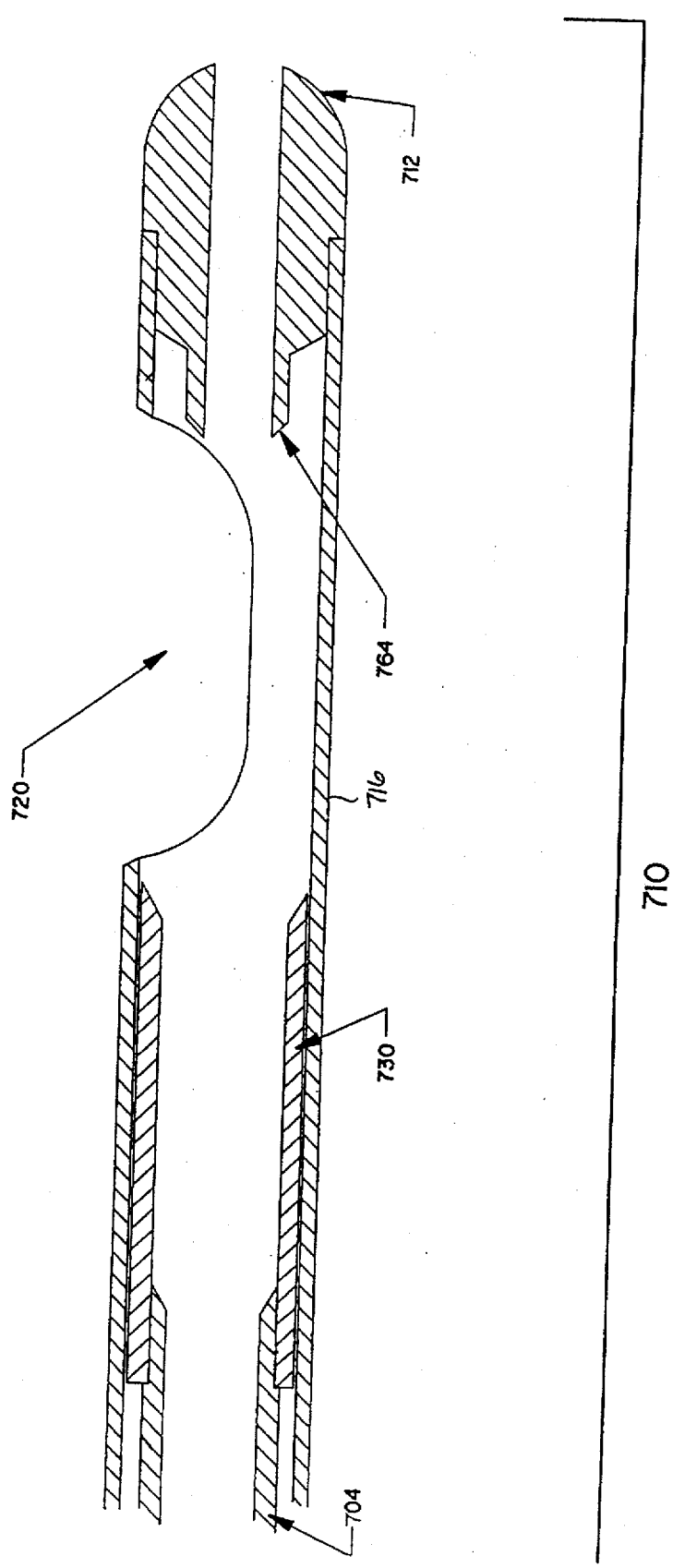
FIG. 7 is a detailed longitudinal section of another embodiment of a housing according to the invention.

Another embodiment, shown in FIG. 7, may be called a tube within a tube. A tube 704 attached to shear 730, is accommodated within an outer tube 716, replacing firing wire 104. The housings of the previously discussed embodiments would have to be adapted to accommodate the tube 704. The inner tube 704 may be connected to a shortened shear 730 or alternatively, tube 704 may be fitted with a sharpened tip preferably formed of chrome in place of shear 730. The tube could be adapted to cooperate with the firing mechanism as will be discussed in regards to FIG. 12.

This embodiment allows for simplified manufacturing. The housing 716, nose cone 712 and extruded tubing extending from housing 716 could all be moulded in one operation while tube 704 is moulded in another operation. In addition, plaque may be pushed into the inner tube 704 by packing stub 764.

A shortened shear as in FIG. 7, allows for more flexibility in the catheter. The use of the embodiment of FIG. 7 allows for improved torqueability and pushability of the catheter housing 710 while in position. Further, with this embodiment a vacuum system may be used whereby a vacuum is applied to the tubing which draws obstructions through the opening, 720 enhancing the removal of the obstruction and removes the excised parts up through the tubing.

The primary shears 230, 330, 430, 530, 630 and 730 are preferably made of stainless steel or chrome, although hard plastics, formed for example by injection moulding, may be satisfactory for cutting some kinds of obstruction. The sharpness of the primary shears should be selected to cut through the hardest obstruction that may be encountered, such as calcified plaque.

The housings 210, 310, 410, 510, 610 and 710 may be made of stainless steel or suitable plastic, and for some applications may be made of flexible plastic. A flexible housing is desirable where the targeted artery is heavily occluded or tortuous such that it would be difficult to penetrate and manoeuver around corners with a rigid housing. Suitable plastics include high density polyurethane, methylpentane polymer, polyethylene tetraphthalate, chlortrifluoroethylene and polycarbonate. Plastics such as PLEXIGLAS™, available from Rohm and Haas Company Of Pennsylvania, and DELRIN™ may also be used.

Each of the housings is preferably tapered and rounded at its forward end to facilitate insertion of the housing into an artery. The size of the housing should be suitable for insertion into arteries and manoeuvering through them. The thickness of the housing should be chosen so that it is sufficiently strong to guide the primary shear and allow for insertion of the housing into an artery, but should not be so thick as to prevent the primary shear from cutting away a reasonable portion (preferably most) of the obstruction. The length of the housing may vary for most applications from 8–25 mm and the outside diameter may vary from 2–5 mm. The length of the shear may vary from 2–12 mm for most applications. Manufacture of the nose cones and tubular sections and their subsequent joining together may be accomplished by any of several known techniques commonly used for the manufacture of catheters for medical applications. A spring useful in the embodiment of FIGS. 3A and 3B, of an appropriate size and strength may be readily commercially obtained.

To enhance the functioning of the catheters of the present invention, stabilizing chambers may be attached to the housing to anchor the catheter in place during use. FIG. 8A illustrates an inflatable anchor 872 which may be manufactured from suitable material and may consist of a number of stabilizing chambers (2 are shown) to position the opening 820 in relation to the obstruction. Such saline anchors 872 may be placed at various positions on the circumference of the housing although the preferred location is directly opposite the opening 820. The preferred embodiment contemplates use of either two, four or six stabilizing chambers 872 as positioned opposite opening 820 according to cross-sectional views taken along X—X and labelled 8Ai, 8Aii and 8Aiii, respectively. These chambers may be situated directly before and after the opening 820, as best seen in plan view 8B, on the underside of the catheter housing 810. As shown in FIG. 8B, these chambers are preferably equally distributed on the underside of the catheter housing where the cross-sections 8Ai, 8Aii and 8Aiii relate to sections through X—X on plan views 8Bi, 8Bii, and 8Biii, respectively. The chambers 872 are filled with a suitable fluid, such as air or preferably saline through tubes 874 which continue to extend between chambers 872. The saline is injected at a port (not shown) adjacent the trigger mechanism.

The inflation of the bladders stabilizes the catheter within the artery to ensure a smooth precise cut. By use of the inflatable anchor on an opposite side of the housing to the opening, the opening will be eased against the artery wall forcing the obstruction into the opening, ensuring the removal of the obstruction as close as possible to its base. The equal distribution of multiple chambers allows a uniform pressure against the artery wall, resulting in a smooth excision of the plaque from the artery wall.

FIG. 9 illustrates the catheter extruded tube as was described in regards to FIG. 7. The catheter extruded tube 979 can be made in various diameters or shapes to suit each individual catheter. The walls of the tube enclose a large central reservoir 977. Formed within the walls are a plurality of lumen 972, 944 and 948 which may accommodate a combination of firing wire 104, guide wire 102, fluid tubes (not shown), and one, two or three stabilizing wires 976. The inclusion of stabilizing wires along the length of the extruded tube prevents tubular stretch when the trigger mechanism is fired. In this way, all of the positive thrust is transmitted to the shear. It is also envisaged that selected lumen of the extruded tubing may transport other materials such as dye, therapeutic agents, coagulants and cauterizing agents. The catheter extruded tube is attached to the housing by various means, ie. swaging, crimping, cold vulcanizing, thermo-welding, while the preferred embodiment would use suitable epoxy cement.

The increased strength of the tube offers the ability to move the housing through very small arteries and around tortuous bends in arteries, allowing the precise location of the cutting surface longitudinally in an artery. Additionally, the ability to apply a rotational force from the firing mechanism to position the cutting surface in the desired radial position in the vessel is offered by the use of a tube. The large reservoir of the tube acts to store excised debris. In addition the extruded tubing allows the guide wire to be extended along a side of the housing through a lumen or monorail rather than through the center of the housing.

Figure 10:
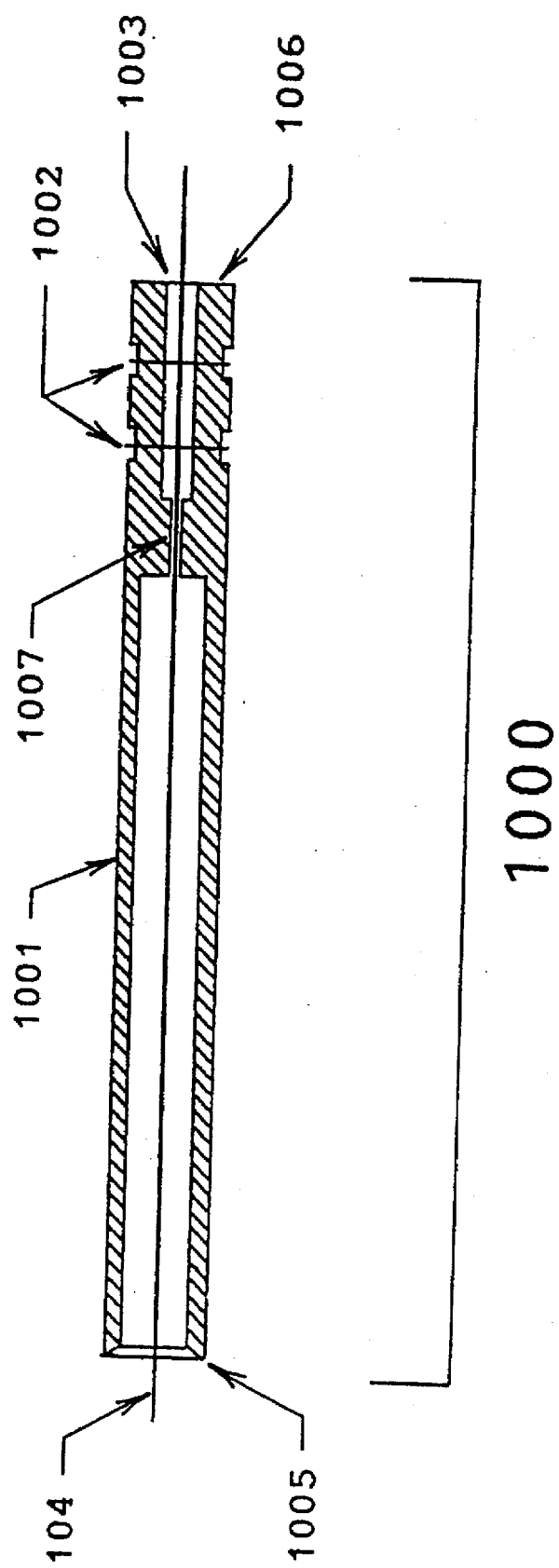
FIG. 10 is a longitudinal section of an embodiment of a catheter adapter according to the invention.

FIG. 10 represents an embodiment of a catheter adapter for attachment adjacent the trigger mechanism, allowing an access port to the extruded tubing. The adapter 1000 is connected at the forward end 1005 to a Y-junction, (such as a Touhy Borst), and at the rearward end 1006, to a snap adapter assembly as will be discussed hereinafter in FIG. 11.

The catheter adapter as shown in FIG. 10 connects a "Y" junction to a snap adapter assembly. The catheter adapter can be maintained between the "Y" junction and the snap adapter assembly in a number of ways. The preferred attachment is a threaded end at 1005 for threaded engagement of a locking grub screw 1203 (shown in FIG. 11) to attach the snap adapter assembly. The preferred is formed from plastic. As can be seen in FIG. 10, the catheter adapter has a central channel 1003 of varying diameter along its length. The central channel accommodates tubes or wires, such as the firing wire 104, before entry into the extruded tube. A catheter adapter intended for accommodation of the firing wire 104, as shown at 1007, to eliminate kinking of firing wire. Preferably, the adapter is threadably engaged to the "Y" junction while a number of grub screws extend through the snap adapter assembly to engage recesses 1002.

The "Y" junction adjacent the forward end 1005 may be used for saline injection into the catheter extruded tube as in FIG. 9, which is transferred to the inflatable saline anchor or anchors as in FIG. 8A. Further, multiple "Y" junctions may be utilized for the introduction of further therapeutic agents or dyes for transport through the extruded tube. Materials that are introduced through the "Y" junction to the tubing may exit the tubing at any point along its length, or at the cutting point of the shear. A "Y" junction could be utilized for introduction of suction line to remove the packed debris from the reservoir of the tubing. Alternatively, a "Y" junction could be used to introduce a wash fluid through the extruded tube to push out or clean packed debris that has been gathered in the reservoir.

Figure 11:
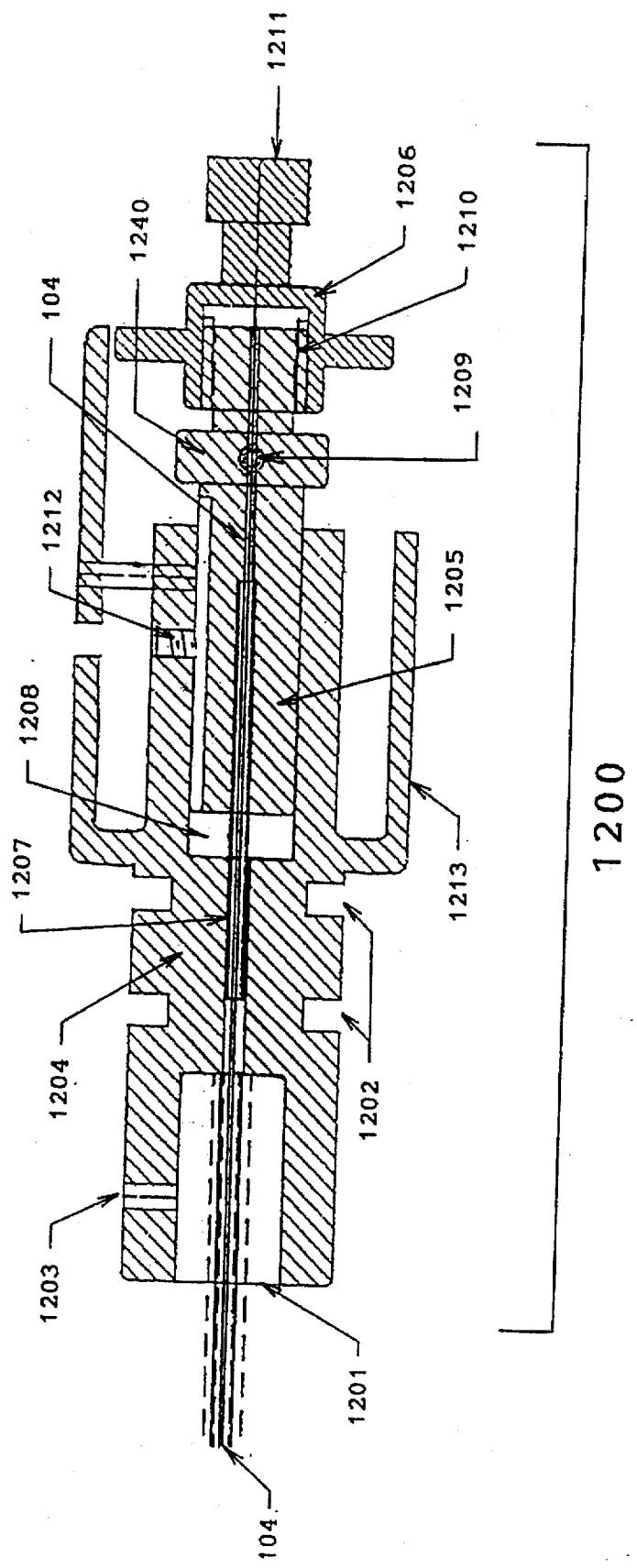
FIG. 11 is a longitudinal section of an embodiment of a snap adapter assembly comprising of many parts according to the invention.

FIG. 11 illustrates a snap adapter assembly 1200. The snap adapter is, in the preferred embodiment, connected between the trigger mechanism and the catheter adapter leading to the extruded tube. The snap adapter 1200 comprises a main body 1204, an adjustable adapter rod 1205, an adapter stud 1211, a guide tube 1207 and a securing point 1209 for the firing wire 104. The forward end of the main body 1204 forms a recess 1201 to accept the catheter adapter, as in FIG. 10, and threaded opening 1203 to accept the means to secure the catheter adapter such as grub screws. The main body 1204 has a plurality of grooves 1202 which allow mating with the firing mechanism as will be discussed in regards to FIG. 12. The outer surface 1213 of the snap adapter assembly can be adapted to provide a higher friction or gripping surface, for example by knurling, to permit the rotation of the snap adapter body which rotation will be transmitted through the extruded tubing to allow the rotation of the housing. The rotation of the adapter through 360 degrees may be accomplished without having to reposition the firing mechanism. The knurl may be calibrated in degrees or some other means to identify the radial location of the housing.

The main body 1204 forms a recess 1208 to accept the adjustable adapter rod 1205. The adjustable adapter rod 1205 is free to move longitudinally within the snap adapter assembly 1200, but can be locked in place by a grub screw extended through threaded opening 1212. The adjustable adapter rod 1205 is free floating so as to allow for the action of the firing mechanism and further to allow for expansion or contraction of the firing wire 104 as it moves through the arteries. Adjustable adapter rod 1205 comprises a flange 1240, containing the securing point 1209 of the firing wire 104. In the preferred embodiment, the firing wire 104 is secured at the adjustable adapter rod 1205 through engagement by grub screws (not shown) extending in from opposite sides the firing wire 104. As shown in FIG. 11, the adjustable adapter rod 1205 contains a guide tube 1207 to accommodate the firing wire and to prevent the kinking or bending of the firing wire 104. The rearward end of the snap adapter assembly is threaded at 1210 to mate with cap 1206 of the adapter stud 1211. Threaded portion 1210 acts with cap 1206 to provide adjustment for the adapter stud 1211, allowing for fine adjustments to the free floating adjustable adapter rod 1205 and thereby adjustments to the length of the firing wire 104. The length of the firing wire determines the range of movement of the shear within the housing. The position of the shear 230 may be determined when in use through the use of a fluoroscope. The adapter stud 1211 is snapped into the firing mechanism, providing positive mechanical connection between a firing pin of the firing mechanism and the shear through the firing wire. The elements of the snap adapter assembly are preferably plastic.

Figure 12:
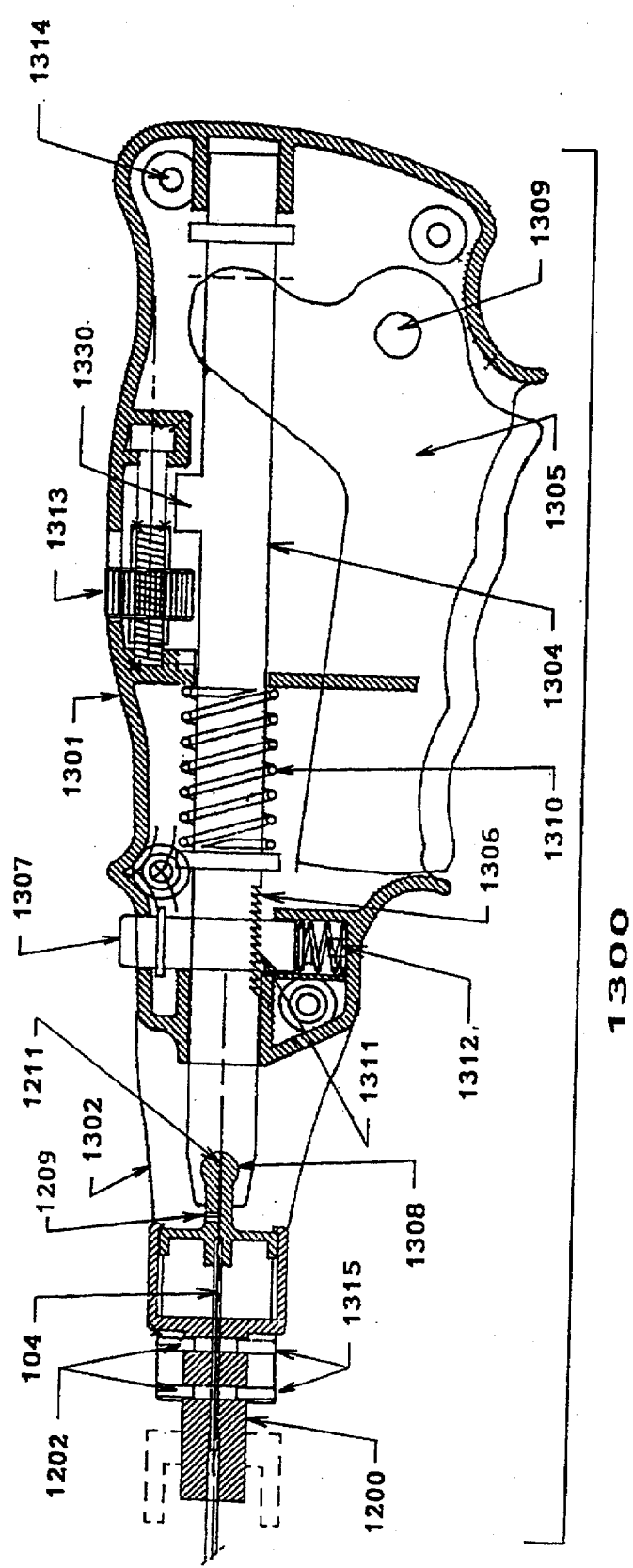
FIG. 12 is a longitudinal section of an embodiment of a firing trigger mechanism according to the invention; and, FIGS. 13A, 13B and 13C longitudinal sections of an embodiment of the endarterectomy catheter mechanics of encapsulation according to the invention.

It is contemplated that the shear mechanism of the catheter may be operated mechanically or hydraulically or by electro-mechanical action (ie. an electrical signal triggering a solenoid). In each such case the firing mechanism design would be governed by the need to transmit the applicable signal or force (ie. hydraulic or electrical, etc.) to the shear. For reasons previously mentioned, the preferred embodiment is a mechanical trigger mechanism for projecting rapid force on release of a trigger as shown in FIG. 12. The force arises from the rapid decompression of a compressed spring. This firing mechanism may be made out of any suitable materials and in any shape as would be envisioned by a man skilled in the art. The preferred trigger mechanism is formed from plastic and is moulded to the users hand.

As shown in FIG. 12, the firing mechanism comprises an outer case 1301 with a snap in receptor bracket 1302. An opposite case (not shown) encloses the mechanics of the firing mechanism and may be welded, screwed or otherwise attached to case 1301 at sites 1314. The mechanics of this firing mechanism comprise a firing pin 1304 having therethrough formed a slot to accommodate a cocking device 1305. A stop 1330 on the pin 1304 determines length of stroke by abutment against adjustable stop 1313. A ratchet 1306 on pin 1304 mates with a trigger release 1311 and holds the firing pin against the forced end of the compressed spring. The pin at the forward end forms a recess 1308 to receive the adapter stud 1211 of the snap adapter assembly as shown in FIG. 11. The mechanics of the firing mechanism further comprises a cam activated cocking device 1305 which pivots on a pin 1309. Cocking device 1305 acts by engagement of the firing pin in extension of the cocking device through the firing pin slot to cause the firing pin to be pulled back and compress firing pin spring 1310 in preparation for firing. The firing pin spring 1310 is carried on the firing pin 1304 and acts between a wall formed on the case 1301 and a flange formed on the firing pin 1304. A trigger 1307 comprises a ratchet portion 1311 which mates with the ratchet 1306 on the firing pin 1304. A spring 1312 at the base of the trigger 1307 maintains the mating of the ratchets until released by the depressing of the trigger 1307 which extends beyond the case 1301.

The snap adapter assembly 1200 snaps into the firing mechanism and is maintained in position by flange 1315 which mate with grooves 1202 on the snap adapter. The adapter stud 1211 fits snugly into the recess 1308 of the firing pin 1304.

In use the snap adapter 1200 is fit into the recess 1308 of the firing pin 1304. The firing mechanism 1300 is cocked by rotating the cocking device 1305 to pull the firing pin 1304 back so that the ratchet portion 1306 of the pin 1304 is engaged with the ratchet portion 1311 of the trigger 1307 In this position the firing pin spring 1310 is compressed between the flange of the firing pin and the wall of the case. Decompression of the spring is prevented by the biasing ratchets together through the trigger spring 1312. It is to be understood that since the firing pin 1304 is directly connected to the adapter rod 1205 (FIG. 11) of the snap adapter 1200 (FIG. 11) (which secures the firing wire), any movement of the pin 1304 is directly transmitted to the wire, 104 which is directly transmitted to the shear. The shear is then displaced rapidly by depressing the trigger 1307 against the trigger spring 1312 which releases the ratchet engagement 1306/1311 and thereby allows rapid decompression of the spring 1310 resulting rapid displacement of the firing pin 1304. The trigger mechanism 1300 provides a comfortable gripping surface with which to manipulate the longitudinal position of the shear. Depending on the application, the characteristics of the spring 1312 mechanism or other means used to provide the energy for the cutting thrust can be adjusted, so as to provide faster or slower or more or less force in the cutting thrust.

The trigger mechanism 1300 is detachable from the housing assemblies so that housing assemblies may be used, disposed of and replaced with sterile catheter assemblies while the trigger assembly may be reused.

The firing wire used in the various embodiments of the invention may be made of any high tensile steel or other material which can transmit a powerful thrust and force repeatedly. The firing wire may also be used in a variety of different diameters, depending on the type of catheter, the size of catheter, and the amount of force being transmitted. Preferably, the diameter ranges from about 0.010" to 0.014". The firing wire can also be of any cross section and may also be of varying lengths, depending on the procedure in which it is going to be used (i.e. heart or fallopian tube or other procedure). The firing wire is attached to the shear at either the forward end or, more preferred, the rearward end. The attachment may be bonded, crimped, snapped or welded. If large enough, the attachment of the firing wire to the shear could be done on a threaded basis, or with two grub screws 1209 pinching the firing wire to the firing mechanism through an attachment called the snap adapter assembly 1300. In the preferred embodiment, the firing wire is welded to the inside of the shear. At the trigger mechanism, it is preferred that two grub screws would pinch the firing wire to the snap adapter assembly as shown in FIG. 11.

The firing wire projects the attached shear positively within the catheter housing with substantial force transferred from the trigger assembly. The result is a quick, smooth and clean cut of the targeted obstruction. In the preferred embodiment, incorporating an extruded tube, the firing wire does not bend or kink as it transmits force to the shear as it is contained within another lumen, as shown in FIG. 9. An alternative is that the firing wire 104 is attached to the shear 230 to pull it back along the housing to excise the debris.

OPERATION OF PREFERRED EMBODIMENTS

Figure 13A:
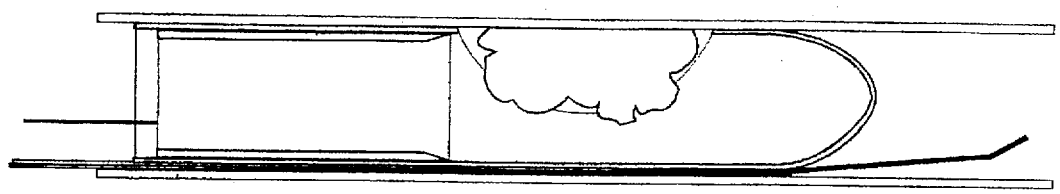
Figure 13B:
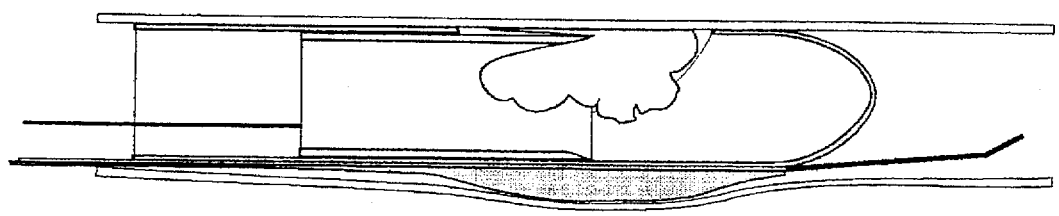
Figure 13C:
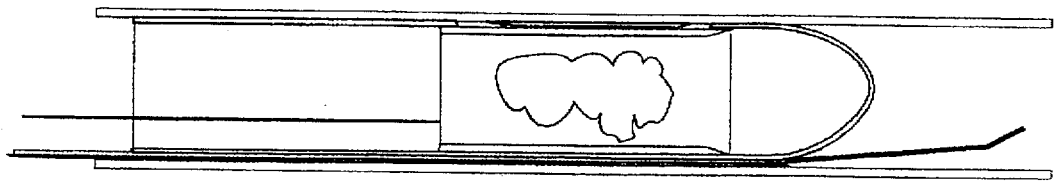

FIG. 13 indicates an example of an arterial view showing the process of the removal of the debris within an artery progressively in views 13A through to 13C.

The catheter of the present invention is located in an artery according to known techniques, such as use of a fluoroscope and dye injected into the artery. In this description, the housing may be selected from the embodiments of FIG. 2 through FIG. 7 or a combination thereof. The location of the targeted obstruction is first identified using known methods. To prevent damage to the artery while the housing is being inserted into the artery, it is preferable that the primary shear be at the forward end of the housing closing or blocking the opening. In this way the cutting edge of the primary shear is effectively sheathed behind the lip of the housing. This is adjusted through adjustment of the length of the firing wire using the adapter stud.

Since the housing may be moveable or fixed along the guide wire the housing may be positioned in two ways. If the housing is moveable along the guide wire a two step process is used. First, the guide wire is inserted slowly into the appropriate artery, then the housing at the end of the wire is then pushed manually along the guide wire about the same distance. This process is repeated until the obstruction is reached. Alternatively, in the fixed housing technique, the guide wire and the housing are fed together into the artery until the obstruction is reached.

As shown in view 14A of FIG. 13, once the location of the obstruction is reached, the housing is oriented so that the obstruction is adjacent the opening in the housing, the primary shear is moved back so that the obstruction may at least partly (and preferably mostly) protrude into the opening. The extent of the obstruction protrusion into the opening will depend in part on the configuration of the opening, for example, the opening may extend around the circumference of the housing. The anchors are inflated to securely position the housing in relation to the obstruction. The trigger may then be operated manually to move the primary shear in the housing to excise the obstruction as shown in view 14B. The shearing action may be repeated if necessary to complete the excision of the obstruction. Therapeutic agents such as a coagulant and/or a cauterizing agent may be injected to the treatment site through the extruded tubing.

In the case of the embodiment shown in FIGS. 3A and 3B, the firing wire 104 may be used to pull the primary shear 330 rearward to compress the spring 350, and then the firing wire 104 may be released so that the spring 350 urges the primary shear 330 forward in the housing 310 to excise the obstruction. The firing wire 104 may also be operated simultaneously with the spring 350 to assist the spring 350 (and vice versa).

The part of the obstruction that is excised by the primary shear falls into the cylindrical body of the primary shear as shown in view 14C and is snagged by the roughened inner surface of the shear. Any debris may also be caught by the screens 252 (if present) or packed into the reservoir by means of the packing stub of various embodiments. If necessary the cutting action of the primary shear may be repeated to remove more of the obstruction. Suction may be applied to pull debris into the reservoir or to remove debris. Alternatively, fivios may be injected to clear debris from the housing.

The primary shear is then held in place blocking the opening while the catheter housing is withdrawn, repositioned or rotated along 360 degrees. If the obstruction has been stored in the catheter, the obstruction may be removed from the housing and discarded or analyzed as desired. Since the catheter is designed to be simple and inexpensive, the catheter may also be discarded.

In some cases, where the obstruction does not protrude into the opening in the housing simply by placement of the housing adjacent the obstruction or the housing is not remaining stationary in the artery, the saline anchor may then be expanded to secure the housing against the wall of the artery over the obstruction so that the obstruction protrudes into the opening of the housing.

A person skilled in the art could make immaterial modifications to the invention described and claimed in this patent without departing from the essence of the invention. The features of the various embodiments as illustrated in the Figures of the invention are intended not to be limiting but to be interchanged depending on the intended use of the catheter.

The catheter could be operated in reverse so that the cutting edge was at the rearward end of the primary shear. Thus the opening could also be oriented more to the rear of the housing. Thus it should be understood that the forward and rearward terminology in the claims may be reversed. However, this is not a preferred manner of operating the catheter. It is preferred that the shear be operated in the direction of the blood flow. Alternatively, the primary shear could be given a degree of rotational movement across the opening but this complicates the operation of the catheter and is not preferred.

Also, the housing and the primary shear need not be cylindrical, although it is considered desirable that the housing have a cross-sectional shape that is similar to that of an artery.

It is important that the primary and secondary shears are sharp enough that they engage and clearly cut the obstruction to prevent the obstruction being simply pushed out of the way during the involvement of the shear. Also, the cables used to operate the primary shear should be stiff enough to exert sufficient force on the primary shear to pierce the obstruction.

The Embodiments of the invention in which an exclusive property or privilege is claimed are defined as follows:

1. A catheter for excising obstructions from within a body channel comprising:
    a housing adapted for entry into the body channel, the housing including a forward end and a rearward end and having an opening for accepting an obstruction;
    a primary shear for cutting the obstruction, the primary shear including a forward end and a rearward end and being disposed within the housing and being moveable forward and backward across the opening;
    an elongated flexible thin solid wire connected to the primary shear and operable from outside the body while the housing is located in the body channel, an urging means cooperable with said elongated flexible thin solid wire to cause propulsive movement of said elongated flexible thin solid wire, release means for holding the urging means in a fixed position, said release means being manually actuatable to release the urging means from the fixed position to propel the elongated flexible thin solid wire to move in one direction without rotation for one stroke only such that the elongated flexible thin solid wire propels the primary shear in the housing in said one direction, without rotation, for said one stroke only toward the forward end of the housing across the opening in a guillotine cutting action; and
    means for locating the housing in the channel.

2. The catheter of claim i wherein the housing is a hollow, substantially cylindrical body.

3. The catheter of claim 2 wherein the housing includes means for allowing free movement of body channel fluid through the housing.

4. The catheter of claim 3 wherein the housing comprises means to prevent the release of parts of the excised obstruction from the housing into the body channel.

5. The catheter of claim 2 wherein the opening extends circumferentially around the housing.

6. The catheter of claim 5 including an inner tubular member in said housing and wherein the forward end is in communication with the rearward end through the inner tubular member.

7. The catheter of claim 6 wherein the primary shear is slidably mounted on the inner tubular member.

8. The catheter of claim 2 wherein the urging means further comprises a spring acting between the rearward end of the housing and the shear.

9. The catheter of claim 2 wherein the primary shear is hollow and substantially cylindrical and fits concentrically within the housing, said primary shear being sized to fit in close proximity to the housing.

10. The catheter of claim 9 wherein the primary shear has a hollow ground cutting edge disposed directly adjacent the housing and the opening is sharpened about its boundaries to enhance the guillotine action.

11. The catheter of claim 9 wherein the primary shear has a roughened inner surface for engaging the excised obstruction.

12. The catheter of claim 9 wherein said opening has a sharpened peripheral portion to form a secondary shear that cooperates with the primary shear when the primary shear moves across the opening to create the guillotine cutting action and wherein a packing stub is provided within the housing spaced from the secondary shear such that the primary shear is receivable in the space between the packing stub and the secondary shear to push and pack the excised parts of the obstruction during the guillotine cutting action.

13. The catheter of claim 2 including a base clamp attached to the primary shear and wherein the elongated flexible thin solid wire is attached to the primary shear by means of the base clamp which acts to distribute the force transmitted by the elongated flexible thin solid wire about the radius of the primary shear and thereby stabilize the movement of the primary shear within the housing.

14. The catheter of claim 13 wherein the base clamp has apertures to allow the free movement of body channel fluids through the base clamp.

15. The catheter of claims 1 including a protective sleeve and wherein the elongated flexible thin solid wire and the means for locating the housing in the channel are accommodated together in the protective sleeve.

16. The catheter of claim 15 wherein the protective sleeve is sized to act as a conduit for a combination of fluid tubes and stabilizing wires.

17. The catheter of claim 15 wherein the rearward end of the housing opens directly into the protective sleeve.

18. The catheter of claim 1 further comprising anchoring means for anchoring the housing within the body channel.

19. The catheter of claim 18 wherein said anchoring means comprises a plurality of fluid fillable bladders disposed about the housing opposite the opening such that said bladders, when filled, urge the opening of the housing toward the obstruction.

20. A method of excising an obstruction from a body channel, the method comprising:

locating a housing within the body channel adjacent an obstruction, the housing having an opening for accepting an obstruction and a shear moveable across the opening;

positioning the housing via a flexible tube such that the obstruction protrudes into the opening of the housing;

urging the shear in a forward direction without rotation for one stroke only toward a forward end of the housing across the opening by means of a longitudinal propulsive force applied to the shear by a flexible thin solid firing wire such that the shear is propelled in a single stroke to excise at least part of the obstruction with a guillotine cutting actions and, removing the housing from the body channel.

* * * * *